(12) United States Patent
Peeters

(10) Patent No.: US 12,229,629 B2
(45) Date of Patent: *Feb. 18, 2025

(54) GENOMIC AND ENVIRONMENTAL BLOCKCHAIN SENSORS

(71) Applicant: John P. Peeters, Williamsburg, VA (US)

(72) Inventor: John P. Peeters, Williamsburg, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/312,605

(22) Filed: May 5, 2023

(65) Prior Publication Data

US 2023/0316022 A1     Oct. 5, 2023

Related U.S. Application Data

(62) Division of application No. 16/560,599, filed on Sep. 4, 2019, now Pat. No. 11,681,886.

(Continued)

(51) Int. Cl.
*A61B 5/00* (2006.01)
*A61B 5/01* (2006.01)
(Continued)

(52) U.S. Cl.
CPC .......... *G06K 7/1413* (2013.01); *A61B 5/0002* (2013.01); *A61B 5/01* (2013.01);
(Continued)

(58) Field of Classification Search
CPC ............. G06K 7/1413; G06K 7/10297; G06K 7/1417; A61B 5/0002; A61B 5/01; A61B 5/1032; A61B 5/14514; A61B 5/14532; A61B 5/1455; A61B 5/442; A61B 5/4833; A61B 5/6833; A61B 2562/0247; A61B 2562/0261; A61B 2562/0271;
(Continued)

(56) References Cited

U.S. PATENT DOCUMENTS 7,148,803 B2 * 12/2006 Bandy ................ G01N 33/0075
340/505
7,969,307 B2   6/2011 Peeters
(Continued)

FOREIGN PATENT DOCUMENTS

EP          2843848 A1    3/2015
WO      WO2015128655 A1  9/2015

OTHER PUBLICATIONS

Mattana; Giorgio, et al.; Recent Advances in Printed Sensors on Foil; Elsevier; Mar. 2016 (12 pages).

*Primary Examiner* — May A Abouelela
(74) *Attorney, Agent, or Firm* — Reising Ethington P.C.

(57) ABSTRACT

A system is described to create customized unique identification (UID) codes combined with customized printable optical or NFC sensors and to combine these unique sensors and unique IDs with unique environmental events, traceability, unique data from cell phones (including geolocation) and person-specific unique indicators such as biomarkers to create completely unique, low cost and proprietary printable genomic and environmental blockchain sensor networks for the Internet of Things (IoT), counterfeit identification, healthcare, pharmaceutical applications and small payment transactions worldwide.

16 Claims, 22 Drawing Sheets

Related U.S. Application Data

(60) Provisional application No. 62/727,589, filed on Sep. 6, 2018.

(51) Int. Cl.

| | | |
|---|---|---|
| *A61B 5/103* | (2006.01) | |
| *A61B 5/145* | (2006.01) | |
| *A61B 5/1455* | (2006.01) | |
| *G01N 33/53* | (2006.01) | |
| *G06K 7/10* | (2006.01) | |
| *G06K 7/14* | (2006.01) | |
| *G06Q 20/40* | (2012.01) | |
| *H04L 9/00* | (2022.01) | |
| *H04N 1/00* | (2006.01) | |

(52) U.S. Cl.
CPC ........ *A61B 5/1032* (2013.01); *A61B 5/14514* (2013.01); *A61B 5/14532* (2013.01); *A61B 5/1455* (2013.01); *A61B 5/442* (2013.01); *A61B 5/4833* (2013.01); *A61B 5/6833* (2013.01); *G01N 33/5302* (2013.01); *G06K 7/10297* (2013.01); *G06K 7/1417* (2013.01); *G06Q 20/401* (2013.01); *H04L 9/50* (2022.05); *H04N 1/00342* (2013.01); *A61B 2562/0247* (2013.01); *A61B 2562/0261* (2013.01); *A61B 2562/0271* (2013.01); *A61B 2562/08* (2013.01)

(58) Field of Classification Search
CPC . A61B 2562/08; A61B 5/1112; A61B 5/0022; A61B 2560/0242; A61B 2562/029; A61B 5/0059; G01N 33/5302; G06Q 20/401; G06Q 10/087; G06Q 2220/00; G06Q 20/02; G06Q 20/0655; G06Q 20/29; G06Q 20/308; G06Q 20/321; G06Q 30/018; G06Q 30/0601; H04L 9/50; H04N 1/00342; H04N 2201/006; H04N 1/00307; G16H 40/67
See application file for complete search history.

(56) References Cited

U.S. PATENT DOCUMENTS

| | | | |
|---|---|---|---|
| 8,035,508 B2* | 10/2011 | Breed .................. H01Q 1/3291 | 709/219 |
| 8,755,839 B2* | 6/2014 | Parkulo ................. G08B 21/16 | 455/457 |
| 9,285,323 B2* | 3/2016 | Burg ....................... G01N 21/79 | |
| 9,311,520 B2 | 4/2016 | Burg et al. | |
| 9,528,941 B2* | 12/2016 | Burg .................. G01N 21/8483 | |
| 9,607,380 B2 | 3/2017 | Burg et al. | |
| 9,863,811 B2 | 1/2018 | Burg | |
| 9,922,281 B2* | 3/2018 | Gabriel .............. G06K 19/0707 | |
| 9,972,077 B2 | 5/2018 | Adiri et al. | |
| 10,002,277 B1* | 6/2018 | Endress ............... G06K 7/1417 | |
| 10,022,614 B1* | 7/2018 | Tran ..................... G16H 50/20 | |
| 10,068,329 B2 | 9/2018 | Adiri et al. | |
| 10,238,288 B2* | 3/2019 | Gupta .................. A61B 5/0006 | |
| 10,267,743 B2 | 4/2019 | Burg et al. | |
| 10,271,738 B2 | 4/2019 | Peeters | |
| 10,323,990 B2* | 6/2019 | Bonifas .................. G01K 1/024 | |
| 10,330,412 B2* | 6/2019 | Gonzalez ............. H01Q 1/2225 | |
| 10,362,984 B2 | 7/2019 | Adiri et al. | |
| 10,368,146 B2* | 7/2019 | Potyrailo ................. H04Q 9/00 | |
| 10,559,081 B2 | 2/2020 | Omer et al. | |
| 10,572,855 B1* | 2/2020 | Levy .................. G06K 19/0723 | |
| 10,602,962 B2* | 3/2020 | Dubielczyk .......... A61B 5/0077 | |
| 10,693,662 B2* | 6/2020 | Nguyen .............. G06Q 10/0833 | |
| 10,719,674 B2* | 7/2020 | Fischer ................ G06K 19/071 | |
| 10,726,214 B2* | 7/2020 | Rein ..................... H04B 17/14 | |
| 10,948,352 B2 | 3/2021 | Burg | |
| 10,983,065 B2 | 4/2021 | Burg et al. | |
| 10,991,096 B2 | 4/2021 | Adiri et al. | |
| 11,026,624 B2 | 6/2021 | Adiri et al. | |
| 11,030,778 B2 | 6/2021 | Burg et al. | |
| 11,087,467 B2 | 8/2021 | Adiri et al. | |
| 11,131,633 B2 | 9/2021 | Burg et al. | |
| 11,158,420 B2* | 10/2021 | Adiri ..................... H04W 12/06 | |
| 11,392,947 B1* | 7/2022 | Prasad ............. G06Q 20/40155 | |
| 11,681,886 B2 | 6/2023 | Peeters | |
| 2006/0290496 A1 | 12/2006 | Peeters | |
| 2007/0162295 A1* | 7/2007 | Akhtar .................... G16H 20/40 | 705/2 |
| 2008/0232653 A1* | 9/2008 | Rowe .................. A61B 5/0062 | 382/124 |
| 2010/0203909 A1* | 8/2010 | Oldach ............... H04L 63/0407 | 709/227 |
| 2013/0303865 A1* | 11/2013 | Rebec .................. A61B 5/0013 | 600/309 |
| 2013/0303869 A1* | 11/2013 | Rebec .................. A61B 5/1459 | 600/365 |
| 2013/0317367 A1* | 11/2013 | Shuler .................. A61B 5/416 | 600/473 |
| 2014/0221847 A1* | 8/2014 | Dubielczyk ........ A61B 5/02055 | 600/479 |
| 2016/0012465 A1* | 1/2016 | Sharp ................... G06Q 20/321 | 705/14.17 |
| 2016/0027042 A1* | 1/2016 | Heeter .............. G06Q 30/0248 | 705/14.47 |
| 2016/0054343 A1* | 2/2016 | Holmes ................ G01N 35/026 | 422/65 |
| 2017/0091397 A1* | 3/2017 | Shah ....................... H04L 63/20 | |
| 2017/0173262 A1* | 6/2017 | Veltz ..................... G16H 20/17 | |
| 2017/0300925 A1* | 10/2017 | Atkinson ................ G06F 3/147 | |
| 2017/0316487 A1* | 11/2017 | Mazed ............... G06Q 30/0241 | |
| 2018/0082024 A1* | 3/2018 | Curbera .................. G06F 21/00 | |
| 2018/0133583 A1* | 5/2018 | Tran .......................... G06F 3/00 | |
| 2018/0336515 A1* | 11/2018 | Mehring ............... H04L 9/3239 | |
| 2019/0046033 A1* | 2/2019 | Gannon .................. G01K 1/024 | |
| 2019/0080127 A1* | 3/2019 | Yoshida ............... G06F 3/04162 | |
| 2019/0165949 A1* | 5/2019 | Ramos ................ G06F 21/6254 | |
| 2019/0207911 A1* | 7/2019 | Wiener ................ H04L 63/0428 | |
| 2019/0272495 A1* | 9/2019 | Moeller ............... G06Q 10/083 | |
| 2019/0272496 A1* | 9/2019 | Moeller ............... G06Q 10/087 | |
| 2019/0370760 A1* | 12/2019 | Kundu .................. H04L 9/3239 | |
| 2020/0027169 A1* | 1/2020 | Valencia ............... H04L 9/3231 | |
| 2020/0034945 A1* | 1/2020 | Soundararajan ...... H04L 9/3271 | |
| 2020/0059467 A1* | 2/2020 | Chereshnev ............ H04L 9/50 | |
| 2020/0082139 A1 | 3/2020 | Peeters | |
| 2020/0129066 A1* | 4/2020 | Gedamu ............... A61B 5/1072 | |
| 2020/0289347 A1* | 9/2020 | Gowans ................ A61M 1/915 | |
| 2021/0146562 A1* | 5/2021 | Panagiotopoulou ......... B26B 21/4031 | |
| 2021/0233672 A1* | 7/2021 | Patil ....................... H04L 63/00 | |

* cited by examiner

GENOMIC AND ENVIRONMENTAL BLOCKCHAIN SENSORS

CROSS-REFERENCE TO RELATED APPLICATIONS

This application is a divisional application of U.S. application Ser. No. 16/560,599 filed on Sep. 4, 2019 and claims the benefit of U.S. Provisional Application No. 62/727,589, filed on Sep. 6, 2018.

STATEMENT REGARDING FEDERALLY SPONSORED RESEARCH

NONE.

STATEMENT REGARDING JOINT DEVELOPMENT AGREEMENT

NONE.

REFERENCE TO SEQUENCING LISTING, TABLE OR COMPUTER PROGRAM LISTING

NONE.

STATEMENT REGARDING PRIOR DISCLOSURES BY THE INVENTOR OR A JOINT INVENTOR UNDER 33 C.F.R 1.77(B)(6)

NONE.

INTRODUCTION

Rapid progress has been made with the resolution and cost reduction of miniature cameras integrated into personal wireless devices such as cell phones, tablets and mini computers. These cameras can now resolve very small printed patterns, including for printable sensors. This ability, combined with the wireless features of cell phones (e.g. communication, processing and geolocation) now creates powerful new opportunities for low cost optical sensors for consumer applications, payments, healthcare, Government, etc. New types of secure, low cost, blockchain networks between consumers and vendors of consumer products are also possible.

BACKGROUND

Optical codes or patterns for product authentication have been used for a long time. For example bar codes were first introduced in Jun. 26, 1974: https://www.smithsonianmag.com/innovation/history-bar-code-180956704/.

An advancement in the art are Quick Response (QR) codes that were invented in 1994 and are now also widely used: https://en.wikipedia.org/wiki/QR_code.

A further advancement was the introduction of Near Field Communication or NFC. Nokia, Philips and Sony established the NFC Forum in 2004: https://en.wikipedia.org/wiki/Near-field_communication.

Blockchain was conceived in 2008 but really started to be deployed in 2016, with blockchain 2.0 and the first worldwide use of cryptocurrencies, e.g. Bitcoin: https://en.wikipedia.org/wiki/Blockchain. One of the issues with Bitcoin is the enormous computer resources required for "mining". Despite the significant level of encryption, Bitcoin exchanges have been hacked. A blockchain is a public or private, permanent, append-only distributed ledger as known to those of skill in the art. Blockchains as a system are believed to be almost completely immune to faking or altering of previously entered data, thus its security level is believed to be extremely high. The blockchain is used to store data or codes in "blocks" that are chained together with each block linked to the previous block cryptographically, each block being encrypted and the entire blockchain distributed to all the computers or nodes that form the blockchain network. New data or codes are always and only added onto the end of the existing blockchain in a new block once it has been confirmed and validated. It serves as a highly secure system of recording "transactions" or data that can be added to but no alteration of previously added data is possible. In creating a block in the blockchain a hash function, a cryptographic tool, turns the data into a string of characters that serve as a virtually unforgeable digital string called a hash. Access to the blockchain and reading of the data requires use of keys to decrypt the data or codes found in the blocks. In the present specification and claims the terms "code(s)" refers to data that can be incorporated into the blocks that form a blockchain. The term "key(s)" refers to the keys used to encrypt, access, decrypt and read data in a blockchain.

More recently QR codes and NFC have been used for payments. Apple has started to use NFC as additional IDs and tokens for payments.

Traceability, item identification to prevent or detect counterfeits, and easy payments are all becoming increasingly important. Also the integration of new, low cost sensors is very desirable, especially for the Internet of Things (IoT) applications.

A next generation technology is now needed to allow universal sensing, improved authentication, traceability, secure payments, health monitoring and consumer interactions (social media) at very low cost and with greater efficiency of computer resources. Simplified private blockchain networks between consumers and vendors are therefore desirable and will allow authentication, small payments and even health monitoring at very low cost.

BRIEF DESCRIPTION OF THE DRAWINGS

FIG. 14A is a disposable patch version and FIG. 14B is a reusable card version according to the present invention;

DETAILED DESCRIPTION

Figure 1:
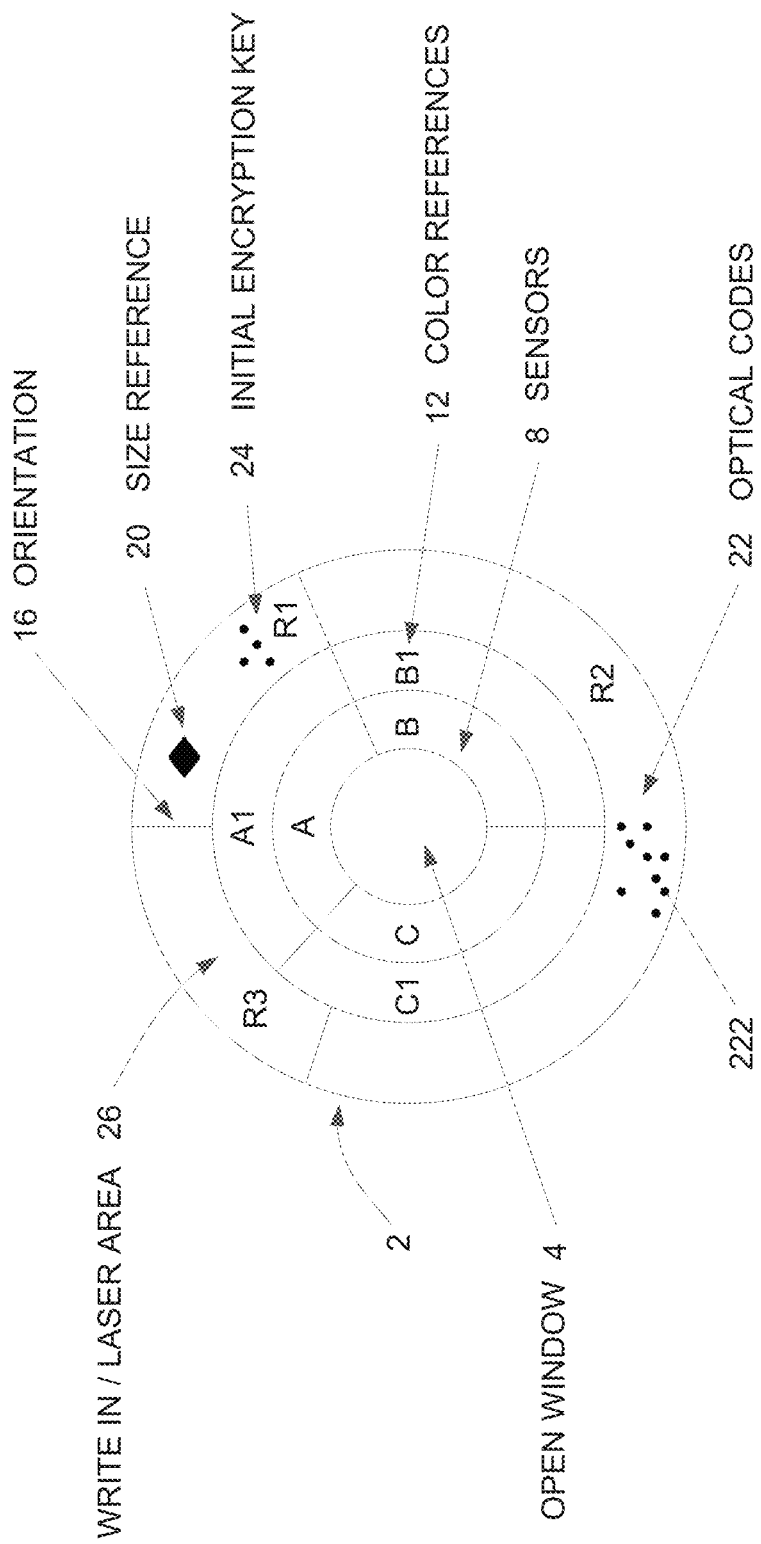
FIG. 1 shows an example of a printable blockchain optical sensor with sensors, reference colors, orientation and encoding system according to the present invention.

Referring to FIG. 1, the printable blockchain optical sensor unit 2 is divided into several printable areas. While the round shape is used and illustrated here, the printable blockchain optical sensor unit 2, generally referred to hereafter as "sensor unit 2", can be of any shape or configuration. Furthermore the sensor unit 2 can be overlaid with any device, market good or application. Although not shown for clarity, the sensor unit 2 generally also includes an adhesive layer to secure the sensor unit 2 to a surface. Such adhesives are known in the art and will not be described further. When the desired surface for attachment is a living surface, such as a skin layer, the adhesive allows the sensor unit 2 to be secured in a removable manner like a band-aid. When the surface is not a living material, for example a package or a consumer good, then the adhesive can be more permanent. For example the sensor unit 2 can be printed on a band-aid, a skin tattoo, a skin patch, a consumer item label or product, a pharmaceutical drug package, etc. and can be overlaid onto a wireless tag, e.g. NFC, Radio Frequency Identification (RFID) or Bluetooth, adding a wireless unique ID (UID) and optional wireless sensor capabilities. It should be noted that when a stand-alone item, such as currency, an identification or payment card or a lateral flow immunoassay are combined with sensor unit 2, the adhesive layer is generally not needed.

Throughout the present specification and claims the term optical sensor is used. An optical sensor is sensor wherein there is a change in the optical properties of the sensor upon "activation" or "detection" of whatever the sensor is designed to detect. The change in optical properties can be a change in color or hue, change in tint, change in tone or change in shade. For the present specification and claims the terms color and hue are used interchangeably. As known to one of skill in the art the hues found on a color wheel are the primary, secondary and tertiary colors. These colors are the following colors going around the wheel: red; red-orange; orange; yellow-orange; yellow; yellow-green; green; blue-green; blue; blue-violet; violet; and red-violet. In a typical artist's color wheel the colors black, white and their combination, which makes grey, are not on the color wheel. Adding white to any color on the color wheel changes its tint, it lightens and desaturates the color. Adding grey, any combination of white and black, to a color on the color wheel changes the tone of the color. Adding black to any color on the color wheel changes its shade. In the present specification and claims a change in color detected by an optical sensor means any change in color, tint, tone or shade and the colors grey, white and black are included in addition to the primary, secondary and tertiary colors found on the color wheel.

In the design illustrated in FIG. 1 the printable blockchain optical sensor unit 2 has an opening 4 in the middle. The purpose of this opening 4, labeled "open window" in FIG. 1, is to allow a surface that is to be measured and authenticated by the sensor unit 2 to be as close as possible to the one or more printable optical sensors 8 on the sensor unit 2. For example if the sensor unit 2 is measuring a parameter on the skin, the skin will appear in the opening 4. Analytes to be measured, for example sweat or biomarkers, can easily migrate to the opening 4. Depending on the materials used for construction of the sensor unit 2, e.g. semi permeable materials, some optical sensors 8 do not need an opening or the opening 4 does not need to be in the center of the sensor unit 2. For some sensor applications, opening 4 is not necessary and it can be replaced by a corporate logo, picture or optical code such as a QR code 136, see FIG. 2B.

Immediately adjacent to opening 4 are the one or more printable optical sensors 8 which together define a sensor area. These optical sensors 8 typically have specific printable chemistries that allow the sensors 8 to change their optical properties following a specific reaction to a given chemical, physical or biological stimulus or exposure to any other parameter that the optical sensor 8 is designed to detect or measure. The printable optical sensors 8 can be a single sensor, a single sensor with a variety of sensitivities divided into separate zones, a number of different sensors or any combination thereof.

A wide range of printable optical sensors 8 are possible and the specific chemistries can be customized for almost any sensor application such as detection or measurement of temperature, moisture, pressure, radiation, the presence of certain chemicals, biologicals, pathogens, etc. or combinations thereof. Specific optical sensors 8, which are typically based on proprietary chemistries, can also be created to identify a unique given person, a location, a chain of custody, a given environment, a biomarker or unique biomarker combinations (biological or genomic signatures) for a given person. Biomarkers can be proteins, DNA, RNA, metabolites, chemicals and stress response indicators present in a bodily fluid or excreta, by way of example only in blood, urine, saliva, sweat, feces, parts thereof and combinations thereof.

The changes in the optical properties of the optical sensors 8 can be reversible, meaning bidirectional, permanent, threshold initiated changes or any combination thereof. For example if the purpose of the optical sensor 8 is to measure ultra violet (UV) sun exposure, the optical sensors 8 can be cumulative and keep changing with increasing exposure, be reversible, be threshold or any combination thereof. Furthermore UV can be divided in UVA and UVB and the specific chemistries and specific colors for the optical sensors 8 produced accordingly. The degree and pace of change itself can be varied depending on the chemistries used for the optical sensor 8. For example a very slow changing chemistry could record a given exposure over a long time, e.g. over a period of weeks, months or even years. Chemistries can also be made to only record threshold exposure events and the degree of the threshold itself can be set by the selection and formulation of the unique printable chemistries for the optical sensor 8. Thus, a change in the optical properties would require a threshold level of the parameter being sensed to be met or exceeded. The combination of printable bidirectional optical sensors, sensors with various degrees of sensitivity and threshold sensors allows precise recording of exposures or events at minimal cost. The sensor area can also include at least one optical sensor 8 that is a timer sensor that changes color in a known way with time, therefore serving as a timer. Printable timer sensors can also record temperature, moisture, exposure to given chemicals or biologicals (e.g. bacteria), etc.

Optical sensor 8 can be composed of inks that can be printed as part of the manufacturing process for sensor unit 2 using a number of standard printing methods well known in the art including screen printing, lithography, flexography, precise deposition methods, e.g. as 3D printing, or other methods. Generally a roll-to-roll manufacturing process is favored for the assembly of more complex sensors.

Sensor inks that change optical properties can be temperature sensitive, referred to as thermochromic, light or UV sensitive referred to as photochromic, moisture sensitive referred to as hydrochromic, can be sensitive to the presence of specific chemicals, to physical agents, e.g. pressure, or can react to the presence of a specific biological agent such as a protein or DNA sequence using specialized attachment and "sandwich" or optical labelling chemistries well known in the art for the manufacturing of lateral flow immunoassays or DNA arrays.

A number of these sensor inks are commercially available from vendors such as LCR Hallcrest (photochromic and thermochromic inks).

Typically the optical sensors 8 are divided in zones or quadrants, illustrated in FIG. 1 as zones A, B and C. While only 3 zones are represented here, many different sensor zones are possible. The technology is suitable for measuring hundreds of parameters simultaneously.

This technology is mainly designed to be used with cell phones or portable wireless devices with a built-in camera and wireless capabilities and is meant to be combined with blockchain technologies.

Figure 2A:
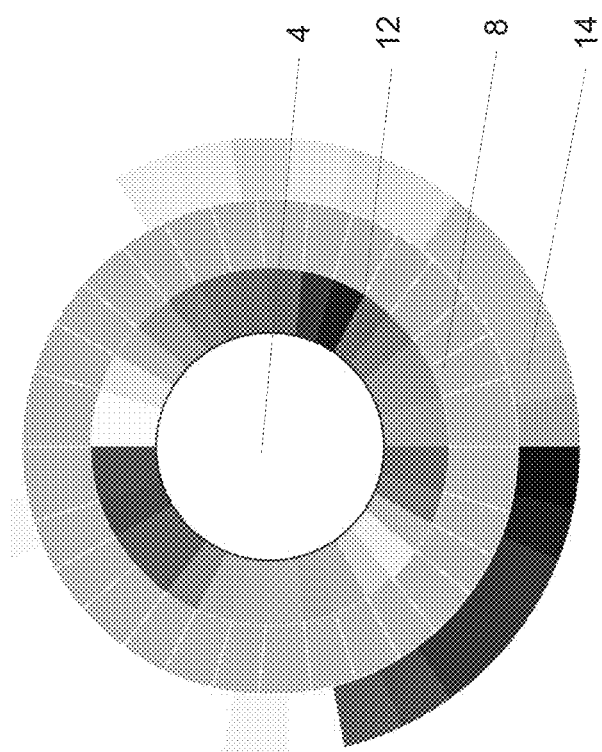
FIG. 2A shows a printable blockchain optical sensor with three separate reference color systems for light correction, sensing and a third application, e.g. skin tones, according to the present invention.

In order to properly read the optical sensor 8 with a cell phone camera, a set of reference colors 12 are provided, see FIGS. 1 and 2A. The reference colors 12 are permanent colors made from inks that do not change or fade with time, and are divided into at least two groups serving two distinct purposes. The first group of reference colors 12 is to allow the camera to calibrate for the ambient light in order to properly read the optical sensors 8. The permanent reference colors, designated as A1, B1 and C1 in FIG. 1, typically include black, white, red, yellow, blue and green. The second group of reference colors includes the references for the colors for the optical sensor 8 itself, meaning the range of possible color changes for the optical sensor 8 as it senses whatever it is designed to detect or monitor. For a more detailed illustration of the optical light reference colors see FIG. 17 12-O, ambient light reference colors and 12-S for sensor 8 reference colors. Thus, the second set of reference colors are used to quantify the change in optical properties of the optical sensor 8 caused by the parameter that is being measured by the optical sensor 8.

For example if the optical sensor 8 is of the magenta color, which is a combination of the colors red and blue, when activated, then the range of colors corresponding to the possible changes in magenta color of the optical sensor 8 might range from light to deep magenta and they would be provided in the second set of printed reference colors for the optical sensor 8. The second set of reference colors allows the optical sensor 8 area to be read precisely and quantitatively based on the correction for the light done with first group of reference colors. In some instances the reference colors 12 will match between the optical sensor 8 colors and the ambient light reference colors and the use of a smaller group of reference colors is then possible.

For some applications multiple printed reference color zones can be used and the order of the zones changed. Also the two reference color sets, for ambient light and the optical sensors 8, can be part of the same ring or reference color area.

For example in FIG. 2A opening 4 is surrounded by the optical reference colors 12 to correct for ambient light and to provide reference colors for the optical sensors 8, then the optical sensors 8 in a ring shape, then another secondary reference color ring 14 which in this instance includes skin tone Pantone® reference colors. The reference color rings 12 and 14 are permanent colors made with inks that do not fade or change with time. Ring-shaped optical sensors 8 represent the sensors whose optical properties vary with exposure to a parameter they are designed to detect.

Therefore this given design, FIG. 2A, allows for ambient light calibration, optical sensor 8 readings and skin tone measurements.

To properly read the optical sensors 8 and reference colors, 12 and 14, the printable blockchain optical sensor unit 2 must also include a means to have its orientation recognized. Referring to FIG. 1, at least one orientation bar 16 can be included and the sensor unit 2 can furthermore include a size reference 20, for example in the shape of a lozenge of defined size, thereby allowing immediate orientation and scaling of the entire sensor unit 2 by the cell phone camera and app. The second reference for orientation and size 20 also allows the direction of the reading of the zones to be determined. The size reference 20 can be of any shape or size desired. Other means of providing orientation and scaling are possible and reference is made to QR code 136 designs as an example. FIG. 2B shows a sensor unit 2 design with a QR code 136 encoded for a direct link to the website www.gentag.com. In this instance orientation of the sensor unit 2 is provided directly by the QR code 136.

Once the sensor unit 2 is properly oriented and the light calibrated then the optical sensor or sensors 8 can be read by the cell phone with remote server authentication possible. Authentication is further possible for any sensor unit 2 by the addition of at least one unique ID, matching a unique printed sensor, pattern, set of chemistries, etc. with an established reference from the manufacturer, as explained below.

Creation of Unique Codes, Encryption and Traceability

In addition to the optical sensors 8 and reference colors 12 and 14, another printable ring 22, FIG. 1, can be added which includes printed optical codes 222. The optical codes 222 can be dots, bars, shapes, patterns, or any combination thereof. The sizes of the bars, dots or shapes themselves can vary, thereby creating almost unlimited number of optical proprietary combinations that can be converted to digits, letters, codes, web links, etc. For example the codes 222 can be circular bar codes.

Figure 3:
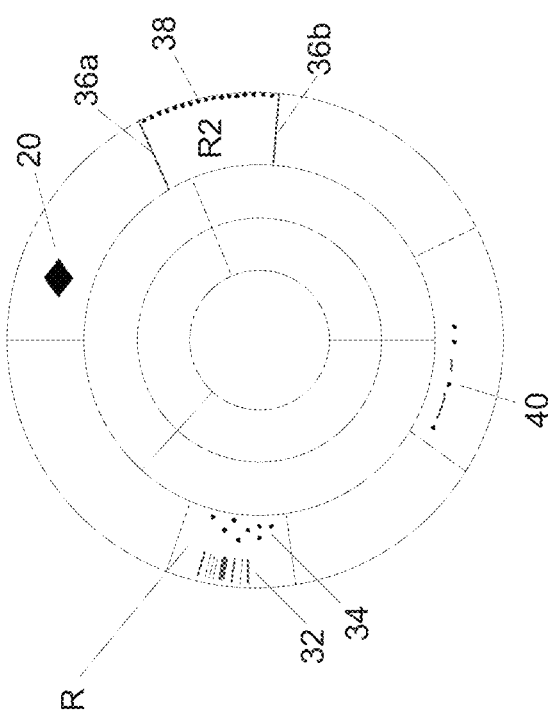
FIG. 3 shows the printable blockchain optical sensor with encoding options for the sensor according to the present invention.

Referring to FIG. 1, codes 222 can be printed within ring 22 in discrete zones or areas see R1, R2, R3, etc. and can be in sequential rings or in a combination as shown in FIG. 3. In FIG. 3 a zone R is separated into two separate sub-rings. Code 32 is a circular bar code and code 34 is a dot pattern code. If a bar code 32 is added then links to the Universal Product Code (UPC) can be added to the sensor unit 2. If a bar code 32 is not added then UPC functionality can also be included using standard encoding methods for QR codes using the printed patterns and keys to decode said patterns or other methods as described below. Sub zones like R can be used for example when the same blockchain optical sensor unit 2 design is used for different brands within the same company and then the sub-rings can contain unique web links for each of the brands.

Any combination of optical shapes, spacing, patterns, colors, color shadings and unique chemistries is possible. For example in FIG. 3 code 40 shows a combination of bars and dots as a coding method. The bars can be of different lengths and thicknesses, like bar codes but circular. Similarly the sizes of the dots or shapes in between the bars can also be varied. A third variable is the spacing patterns, creating an almost unlimited number of possible optical combinations and codes.

The shapes can include variations for given shapes to allow correction for read angles. While not shown here colors can also be used in zones R and color shading can be used to create yet a further level of unique printable codes and patterns.

Typically at least 5 zones R are provided for coding. The zones R can be numbered by their distance from the orientation bar 16 and size reference 20 and can be read clockwise or counter-clockwise. The more optical R zones and the more patterns and the higher the printing density, the more sophisticated the technology.

If the blockchain optical sensor unit 2 uses zones R for the codes then a blank zone 26, FIG. 1 zone R3, can be set aside and can serve several purposes. It can be used to further encode dots or patterns using laser printing for example of dots or shapes to encode for example new UIDs, unique shipment information events, unique sensing events and chain of custody information from manufacturing to point of sale to the consumer. The blank zone 26 can also be used to write in or print a name, for example of a child.

Information encoded in these optical codes and zones R can include: a web or hyperlink, metadata unique to the product such as a date and time of manufacture, a unique serial number, a unique item ID, other unique numbers or keys, information to decode the label or sensor, web links and access codes, encryption keys, and other information (e.g. personal information). A given zone R can include random codes for cross validation purposes, sub-zones and the creation of a series of unique encryption keys. Random codes and patterns can be used as unique identifiers to confuse counterfeiters.

For example zone R1 can include a first encryption key 24, FIG. 1, that defines how the other R zones should be read, in what order, the presence and location of sub-zones and how they are encoded. A given zone or block can contain random codes and the position of these zones can also be defined by the first encryption key 24 in zone R1. As noted above, a QR, bar, or other optical codes can be used as an alternative to a customized first encryption key 24 and the use of customized optical codes 222 and R zones, FIG. 1.

Referring to FIG. 3, the position of a given key or code can be defined in relation to size reference 20 and a start bar 36a that can define the start of a given zone, for example R2. A given zone can be ended by an end bar 36b. Furthermore zones can include sub-zone position markers 38, spaced equally within a zone. Since position markers 38 are equally spaced they can also serve as means to optically measure something, see the example below for melanoma. Dots or printed patterns can be selectively read only in certain zones defined by the keys.

A first encryption key 24, FIG. 1, can generate another encryption key and the process can be repeated multiple times to achieve a high level of encryption. For example first encryption key 24 can indicate the location of a second encryption key located in another zone (e.g. R2) in a given position defined by position markers 38. New keys or codes can be added in zone R3 and keys can be hidden in certain zones. Keys or decryption codes can also be located remotely on servers whose web address and access codes are located and defined by the printable codes. Rolling codes and tokens can be used on said servers to further make the breaking of the printable keys extremely difficult. Keys can be part of a blockchain wallet and can include both private and public keys. Public or private blockchains can be used or combined. The technology can be used with cryptographic randomized information dispersal algorithms combined with Android cell phones such as that from Trivalent at www.trivalent.com.

Hidden Sensor Blockchain Keys

The use of printable chemistries allows additional encryption and functionality. For example a zone R with specific keys, codes or a message can be printed with temperature sensitive inks that reveal an optical code only at a given temperature (e.g. using a fingertip). Similarly certain zones R can reveal dots or patterns only in the presence of certain chemicals, certain proteins, specific DNA sequences, bacteria or physical agents.

Keys can also be activated by the presence of certain biomarkers, for example found in the sweat on a finger of a person to create person-specific keys, codes or tokens. An example is a disease-specific biomarker code, for example for a person with diabetes. Keys can be activated also by certain proprietary chemistries, creating a further level of security and uniqueness. For example a warehouse might contain a non-toxic signature chemical that will activate a printable key only in the presence of said chemical, thereby proving that that an item was present in that location. In addition keys can be printed in zones R with inks that will fade over a given time period (e.g. a day) so that the device can only be used within a given time period and within a given location (e.g. an amusement park). Keys can also decode how a given sensor should be read and interpreted. Therefore this technology contains self-recording encrypted features that can form part of a self-contained or shared blockchain ledger.

Use of RFID or NFC

Figure 4:
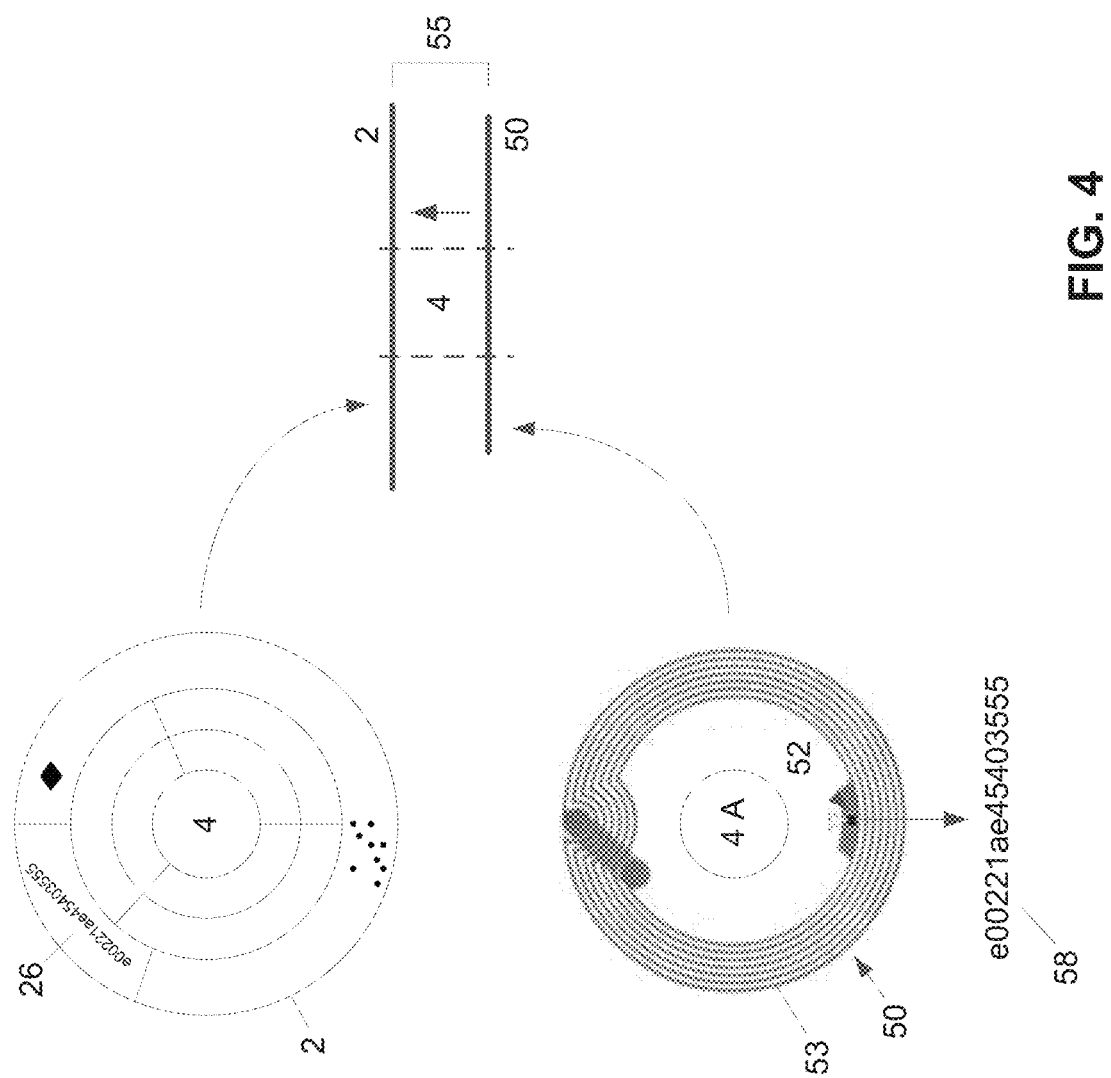
FIG. 4 shows the printable blockchain optical sensor overlaid onto an RFID or NFC tag to form a combined sensor unit according to the present invention.

Unique optical keys and numbers can match other unique IDs for example from an RFID or NFC tag or NFC sensor unit 50 that contains a chip 52 and an antenna 53, see FIG. 4. Said NFC tag or sensor unit 50 itself has a unique permanent "hard" ID 58. The unique IDs (UIDs) of NFC tags are totally unique by international standards, making the technology very useful for blockchain sensor networks. As explained in earlier patents by the same inventor NFC can be used for payments, see for example U.S. Pat. No. 7,148,803.

As shown in FIG. 4, the NFC tag or NFC sensor unit 50 can be overlaid directly onto a printable blockchain optical sensor unit 2, forming a combined unit 55. Opening 4A can be made for the NFC tag or sensor unit 50 matching exactly opening 4 of sensor unit 2. NFC antennas and even basic chips are themselves printable but in this instance both NFC with traditional silicon and printable NFC technologies are contemplated. NFC adds functionality that is complementary to the optical technologies and in some applications can reduce or eliminate the uses of optical codes 222, R zones and the first encryption key 24.

If NFC is added to the blockchain optical sensor unit 2 then additional cross validation of unique numbers and codes becomes available and sophisticated anti-counterfeit and blockchain applications are possible. For example the UID of the NFC tag or sensor 50 can be printed or coded in the write in blank zone 26 as a means to cross check and authenticate printable blockchain optical sensor unit 2 directly by a consumer using the cell phone to read the NFC tag ID using an app such as NFC TagInfo from NFC Research Lab Hagenberg. Further codes can be programmed or written into the write area of the NFC tag itself beyond the hard ID 58. Remote storage of the additional codes, cell phone read transactions timestamps, locations, unique keys and tokens are also possible.

Figure 5:
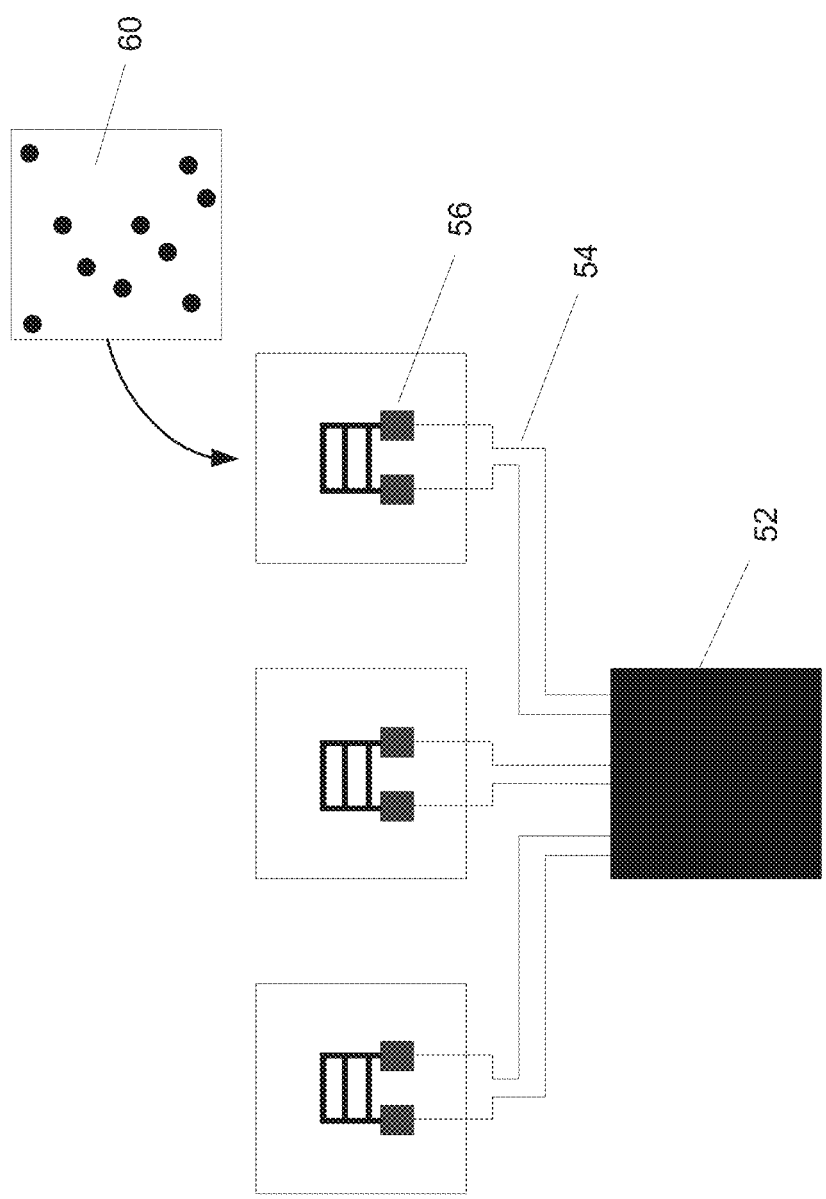
FIG. 5 shows an NFC tag as shown in FIG. 4 further comprising printed leads, micro-heaters and optical micropatterns in accordance with the present invention.

Furthermore with NFC sophisticated additional optical authentication technologies are possible, see FIG. 5 showing a further modification of FIG. 4. For example a customized NFC application-specific integrated circuit (ASIC) can be made with printable leads 54 FIG. 5. Said leads 54 can terminate in tiny printable micro-heaters 56 located in a zone R that can be overlaid for example with a temperature sensitive ink with micro patterns 60 that appear only upon activation of said micro-heaters 56. A plurality of one-time use micro-heaters 56 can be printed and create optical zones that are sequential and indicate how many times the NFC tag has been read in transit.

Reading of the NFC hard ID 58 in transit as part of a remote blockchain system allows cross validation at the point of sale with the visual read of the optical micropatterns 60 described in FIG. 5.

The use of NFC sensors and printed sensor leads 54 to determine for example if an item has been opened or tampered with is well known. Reference is made to U.S. Pat. Nos. 7,148,803; 7,969,307 and 10,271,738 and derivations from the same author, that are incorporated herein in their entirety.

For example a printed loop from the NFC ASIC can serve to indicate if an item has been opened, if a pressure inside an item has changed, if a contaminant is present, etc.

While the above describes NFC, Bluetooth or other chip technologies can also be used. Preferentially the technology should be low cost, battery-less and unique.

Custom ASICS

In addition to the proprietary printed optical technologies described above, custom NFC or Bluetooth application-specific integrated circuits (ASICs) can be produced and customized for unique proprietary sensor applications and ASIC designs as unique microchips. Such ASICs can be made by companies such as NXP Semiconductors, Texas Instruments, STMicroelectronics, or a number of smaller specialized firms. Customization of ASICs allows for the ownership of the unique IDs of each chip, incorporated in each item or combined unit 55. This is akin to the credit card model where unique codes are generated for each card but applied to proprietary sensors.

The custom chips can also be further modified to include a proprietary rolling code token generator, encryption stacks, etc. The internal Unique ID (UID) of each given ASIC can be linked to given code decryption keys on remote servers, creating an even higher level of security for blockchain and other IoT applications.

Combined Optical and Electro-Chemical Sensors

The use of printable optical chemistries allows for a wide range of simple sensing applications, including for detection of proteins and even DNA. For example lateral flow immunoassays are protein detection technologies that are generally optical, low cost and quite accurate.

In some instances it is desirable to include an electro-chemical sensor that can be considerably more accurate than a simple chemical optical sensor. Such sensors can be NFC sensors, which can be battery-less and where power is provided remotely from for example a cell phone. Bluetooth and other wireless ASICs can also be used. For further details on NFC sensors see U.S. Pat. No. 7,148,803.

NFC and the electro-chemical sensing layers add considerable sophistication to the optical sensor 8 technology. For example as indicated in FIG. 5, the NFC technology (ASIC) can be modified to add internal and external sensors or devices. In one application, as indicated above, a custom NFC ASIC can activate a printable area and reveal codes after a first reading of the NFC chip. Printed zones R can include such layers that then indicate the number of times a given item has been read by NFC, as a further validation and cross reference technology. Web link directors can be added to the ASIC such that any cell phone read or transaction records the unique ID of the cell phone, the location, timestamp, sensing events, etc. and sends this information to a remote encrypted web database, server or blockchain network.

In the example above activation of printed patterns can be done by NFC. Optical, non-NFC, patterns can also appear for certain exposures, e.g. to temperature. For example a label for a vaccine or drug that is sensitive to temperature can include zone R areas that reveal a printed code pattern only if the label has been exposed to a certain temperature. Similarly printed patterns in zone R can record exposures to certain chemicals, biologicals, etc. providing a low cost optical record of shipment, handling and location. The hard optical codes that are created on the sensor unit 2 itself can then be cross validated with the traceability or blockchain codes on the encrypted blockchain network.

NFC anti-tampering sensor loops are very useful. The use of electro-chemical sensors further allows for sophisticated authentication and security, notably by the use of unique custom chemistries. Examples of authentication include sweat composition, biomarkers, the detection of unique proteins, DNA or given chemicals. These are very useful for geographical, genomic, ethnical, medical or pharmaceutical cross validation applications.

Addition of Microneedles

Figure 6:
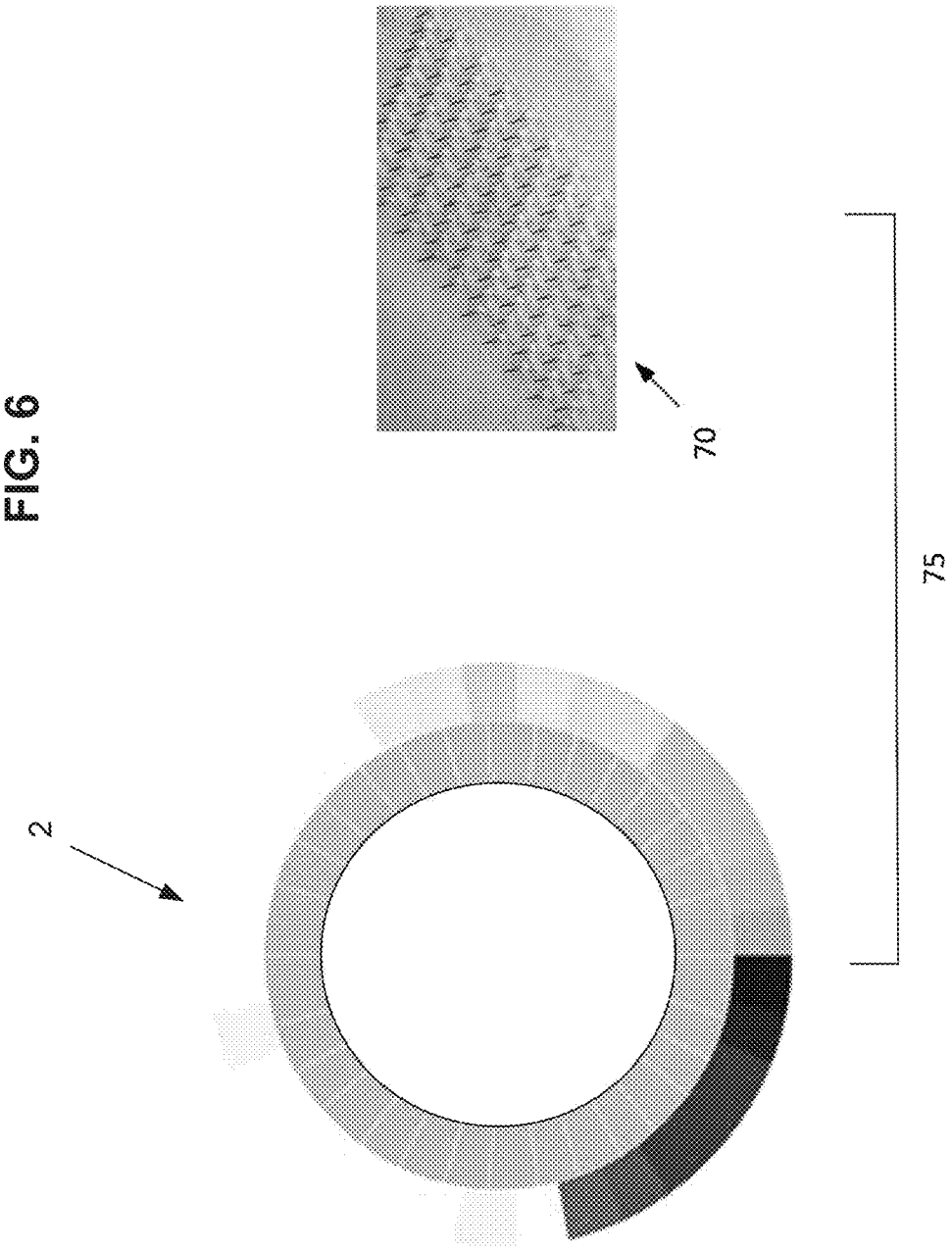
FIG. 6 shows a combination of a printable blockchain optical sensor with a means to extract a fluid sample from a surface via the addition of microneedles according to the present invention.

In another application a printable blockchain optical sensor unit 2 is combined with a layer of microneedles 70, typically placed under the sensor unit 2 and under the NFC layer, if present, and with the microneedles 70 oriented in the opposite direction from the optical sensors 8 and reference colors 12 and 14, forming a combined sensor unit 75, see FIG. 6. Combined sensor unit 75 can include, optionally, an NFC layer with electro-chemical sensors, thereby creating a combined optical and electro-chemical sensor device. It should be noted that optical codes are not shown in FIG. 6 for the sake of clarity.

In one application the combined sensor unit 75 can be depressed on a surface to draw fluid onto the sensor unit 75. In one application the surface is the skin of the person and the fluid is interstitial fluid. In one further application the combined sensor unit 75 forms a disposable optical or combined optical and electro-chemical wireless diabetes patch for measuring interstitial glucose levels in a user.

The technology, either optical, electro-chemical or a combination thereof can be used for any biomarker detection, detection of pathogens in a package, detection of DNA, etc. The technology can furthermore include authentication of the patch, payment, geolocation via the cell phone, emergency care, telemedicine, etc.

Biomarkers can be used to authenticate an ethnic group or an individual person, adding a further unique layer of authentication.

The above technologies can be printed by standards methods. NFC can be added by roll-to-roll printed and assembly processes that are well known in the art.

In a variation of the design shown in FIG. 6, a skin patch sensor unit typically without the microneedle layer can be made just as for sensor unit 2 with an opening in the center, optical codes and optical sensors 8 and the addition of a wireless application-specific integrated circuit (ASIC) or chip 52 for sensor measurements that can include temperature, pressure or alternatively stretching of the skin patch, and other optional variables. It is designated as a skin patch sensor unit because it is designed to be worn on the skin, thus it includes an adhesive (not shown) to removably secure it to the skin, however the technology and features it can include remain the same as the sensor units 2 described herein elsewhere. Such adhesives are well known in the medical art, band-aid art and first aid art and thus will not be further described.

In one application the skin patch type sensor unit serves as a means to detect an injection of a biosimilar or biological drug and is a drug compliance blockchain sensor unit 2. The open center 4 of the skin patch sensor unit 2 allows for a clear insertion of a needle to deliver a drug by a patient or user of the drug. The sensor unit 2 detects the localized skin swelling caused by the insertion of the needle resulting in small, but measurable changes of localized pressure/skin stretching and changes in localized skin temperature. These changes can be measured by the ASIC by precise thermistors and pressure or stretch sensors integrated in the patch. The ASIC then can transmit the data to a cell phone and the entire system can form part of a secure network and blockchain system.

The optical sensors 8 may include temperature sensitive inks that can confirm optically via a cell phone that the skin patch sensor unit 2 is worn on the skin. This way when the skin patch sensor unit 2 is read and authenticated, further validation can be provided by means of the picture that shows the skin patch correctly applied on the skin. The injection site can be visible on the picture and form a further part of the authentication system that includes the UID of the skin patch, the location, the UID of the user cell phone, optical validation codes, sensor validation codes, and a blockchain network.

Different design and sensor variations are possible for a blockchain drug delivery and/or compliance skin patch that includes the sensor unit 2. For example the drug compliance skin patch can include a means of directly sensing the needle insertion through the skin patch as an alternative to insertion in an open area in the center of the skin patch. Such sensing can be optical, for example by the needle insertion causing piercing and mixing of a non-toxic optical ink, creating a pre-defined pattern on the skin patch and forming a part of the authentication system. The pre-defined optical pattern is then read by the camera of the wireless reader such as a cell phone and the information communicated to the blockchain network. Alternatively the piercing can release a conductive liquid, closing a sensor loop in the patch and in this case the patch would include an ASIC.

The blockchain drug compliance patch can include other optical sensors 8, such as biomarker sensors associated with the drug. The drug compliance blockchain skin patches can be stand-alone optical sensors 8, be based on an ASIC or be a combination thereof.

Markets for the optical blockchain drug compliance patch include the injectable drugs adalimumab (or Humira) and etanercept (or Enbrel), generics of these pharmaceuticals and biosimilars to them. Many other markets exist for this technology and include for example the current biologic asthma drugs sold under the names of Dupixent, Nucala, Fasenra and Cinqair. The drug compliance patch technology can be used for biosimilars, biologics or any other drugs or treatments that are injected in the skin.

Initial Set of Unique Blockchain Codes

One of the objectives of this invention is to allow easy and universal printing of optical sensor units 2 and then the overlaying of these sensor units 2 with conventional blockchain applications like chain of custody and payment information blockchain networks.

The printing of unique codes and/or the integration of NFC is explained above. This section explains how unique codes can form unique code blocks that can be encrypted and form a sensor blockchain system and network.

Many of the applications described herein are meant for small consumer transactions, authentication and low cost wireless transactions.

The use of the unique customized codes allows authentication and small payments by creating either custom networks or by using existing or emerging systems, such as NFC payments.

Figure 7:
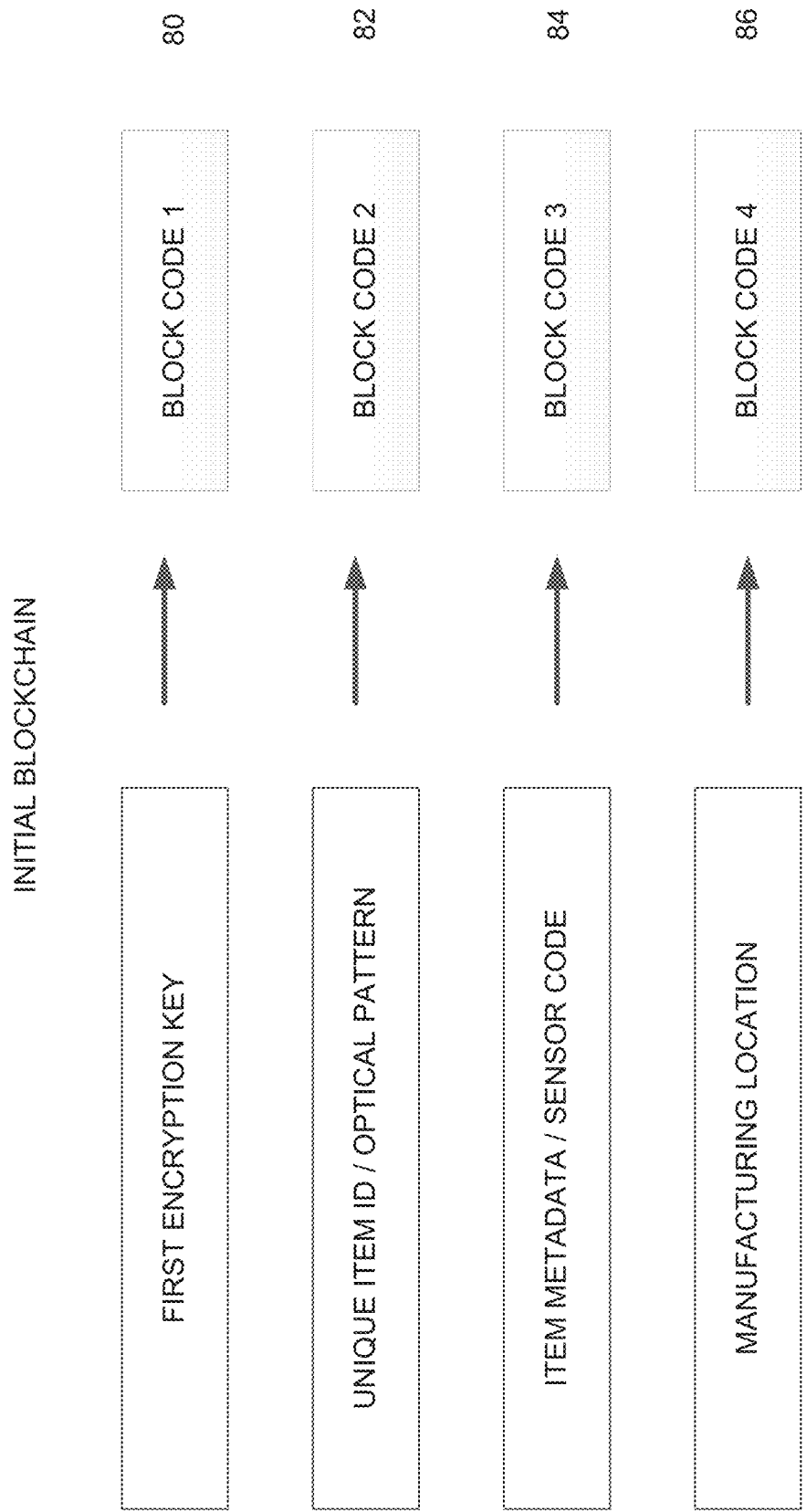
FIG. 7 is a schematic diagram showing creation of a first set of unique blockchain sensor IDs and keys for the initial blockchain system associated with a unique item, sensor or device according to the present invention.

FIG. 7 illustrates the creation of the first set of blockchain sensor keys and IDs and the establishment of the initial blockchain network.

As stated above either public, semipublic, private or custom blockchain networks can be used. For example the Ethereum blockchain can be used and combined with other payment blockchains such as PayPal®, Master Card®, Visa® or Apple Pay®. Alternatively a large company can create its own totally proprietary blockchain sensor network or networks as explained below.

The initial blockchain network block can include block code 1 (80), FIG. 7, that can include the initial first encryption key 24 of the printed blockchain optical sensor unit 2 or other unique keys or codes described above, including the UID of an NFC tag or sensor, if included.

Block code 2 (82) can include the item UID as defined by printed optical codes 222, unique printed patterns of printed blockchain optical sensor unit 2 or further IDs encoded in the NFC tag or sensor.

Block code 3 (84) can include the item metadata and the unique sensor data codes.

Block code 4 (86) can include a unique code for the manufacturing location and/or the target sale location for the item.

In this initial set of codes which typically are encrypted, block codes 1-3 can serve as the private key to a wallet and block code 4 as the first part of the public key for a distributed ledger, i.e. the blockchain for the sensor unit 2, depending on the application.

Since sophisticated encryption is possible, particularly with the overlay of NFC, codes can be used for URL redirection, metadata transfer, etc. Other keys and tokens can be on remote servers and any cybersecurity or cryptographic technology can be used for added network protection. The technology can be also used to make small micro-payments and transactions for almost any consumer market.

A second set of blockchain codes, i.e. another block in the blockchain, is created the traditional way by reading and coding the shipping and chain of custody information of the item. There are a number of well-established tracking technologies and blockchain systems currently used for chain of custody. Typically location, arrival and departure time, particular custodian, etc. are coded. Reference is made to systems such as Fedex, the US postal system, Walmart, Amazon, etc. The technology described here further adds sensor data and unique resulting keys to the blockchain information.

It is important to note that various degrees of sophistication and encryption are possible with this blockchain technology. Extensive encryption like Bitcoin require considerable computing resources, which, for most applications described herein, are not necessary or desirable.

For most consumer market applications a simplified custom blockchain is possible and can even be placed on existing systems or networks (e.g. Google).

The above technology allows great flexibility. The printable zones R can define multiple access points to a blockchain and creates multiple unique and proprietary codes from the onset. For example a customized tracking chain could be placed on one network and be accessed via codes in one zone R. Another zone R could define access to a second network, for example for payments. NFC further allows wireless coding, unique IDs, storage of unique information, creation of rolling codes, storage of location data and the use of unique sensors.

The use of sensors and codes that are revealed only in certain circumstances specifically allows the overlay of blockchain technologies with sensors.

Figure 21:
FIG. 21 shows a schematic block diagram of creation of a shipment block code sequence according to the present invention.

For example in the chain of custody for shipment from a manufacturing point to a distribution point unique T codes, for transport, are created. Unique codes include location, timestamp, UID of readers, truck ID, ID of staff, etc. Each code can be encrypted as they are incorporated into the blockchain. The addition of sensors in the sequence chain T allows completely unique and proprietary validation points. For example in position 2 (block code 2) in the chain shown in FIG. 7, a reading can be requested of NFC with the creation of a shipment block R creating an optical code for that position, as explained in FIG. 5 and as illustrated in FIG. 21 by a darker middle box.

Similarly if no NFC is used then items for position 2 (FIG. 7) can be exposed to a given chemical or physical exposure, revealing a new and unique optical code in a given zone R for that shipment point.

This knowledge together with the unique codes, patterns and chemistries are known only to the owner of the original sensor unit. Depending on the value of the item the option then exists to overlay this technology with sophisticated external blockchain networks.

Third Set of Unique Blockchain Codes

Figure 8:
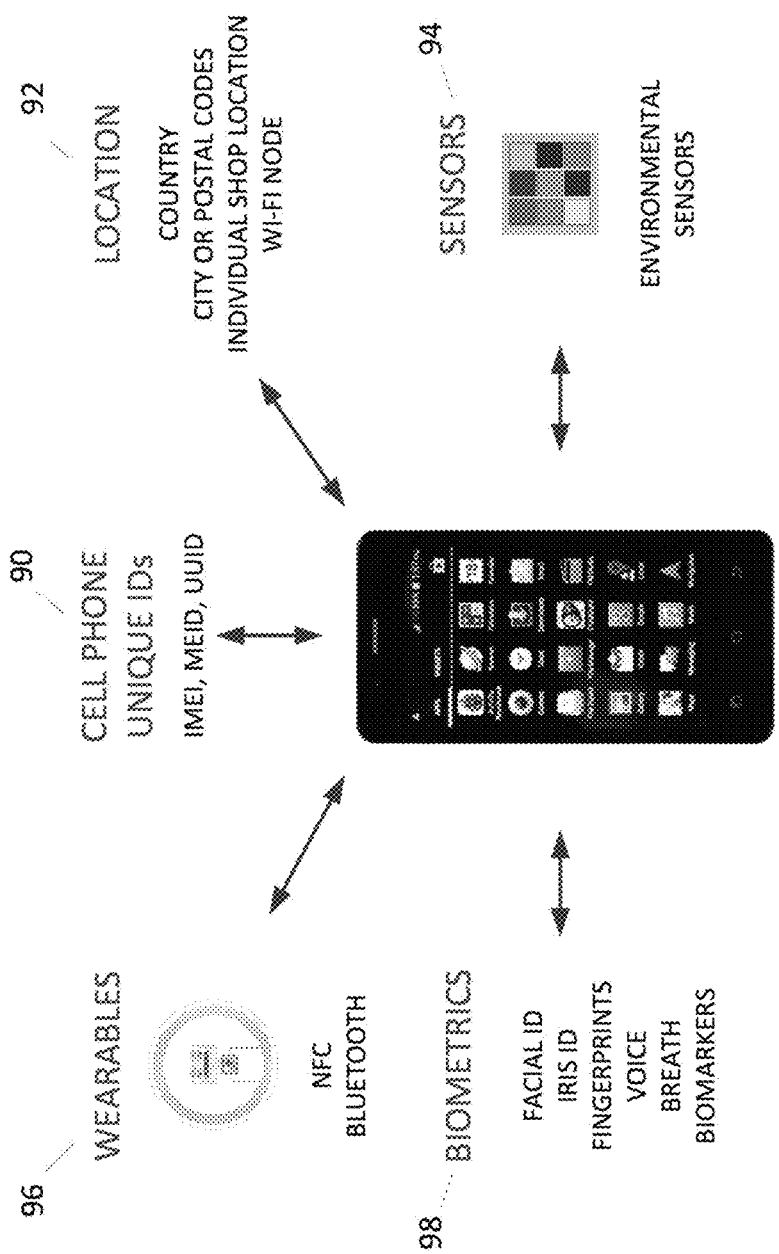
FIG. 8 is a schematic diagram showing the unique IDs, keys and optical sensors that can be associated with a consumer cell phone according to the present invention.
Figure 9:
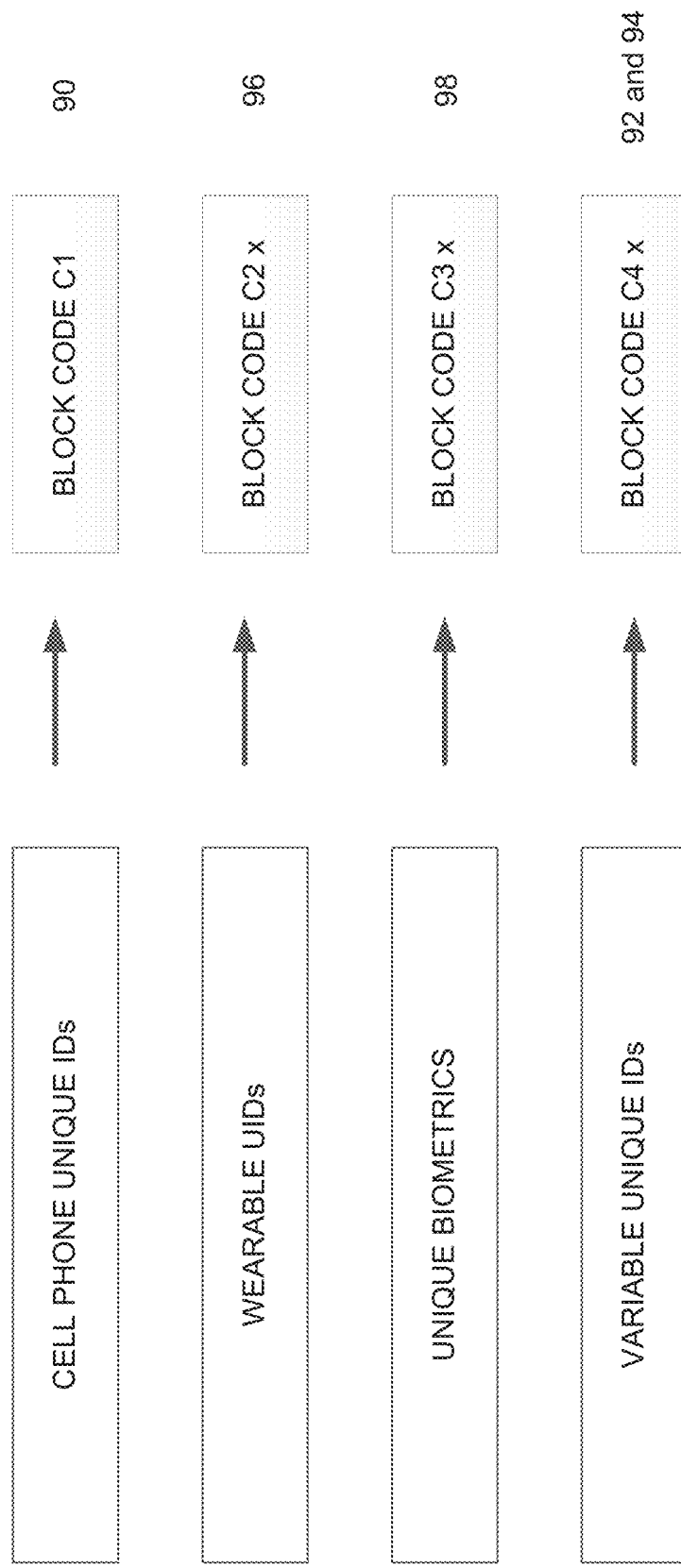
FIG. 9 is a schematic diagram showing examples of unique resulting blockchain ID codes that can result from the system shown in FIG. 8 according to the present invention.

Cell phones contain their own set of unique IDs (e.g. IMEI, MEID, UUID numbers) and their use with this technology together with sensor units 2 creates a large number of further unique IDs and codes that can be incorporated into the blockchain, as described in FIGS. 8 and 9.

Specifically the cell phone of the consumer wanting to authenticate or use the item with blockchain optical sensor unit 2 has its own set of unique codes, creating a further block code 90. In addition the user may wear a Bluetooth or NFC accessory (e.g. Fitbit, an earpiece, etc.), itself with a chip with a unique ID, creating another unique block code 96. Blocks 90 and 96 can be combined and create a completely unique encrypted consumer code or ID. This code is universal and completely unique for each person worldwide. The consumer cell phone can also be used to create a location code 92 related to a determined geolocation such as a country, city, postal zone, building location, Wi-Fi node location or a geographical quadrant. The consumer cell phone can also include environmental sensors to create a variable environmental code 94.

A user also has a unique set of biometrics 98, each of which can be converted to a further unique set of codes for incorporation into the blockchain. Biometric codes can be permanent or be variable. Examples of permanent unique biometric codes are fingerprints, iris patterns, facial patterns and generally voice. All of these can be readily captured by smartphones. Some biomarker patterns are also unique to the person (e.g. genome) or can reflect a health status (e.g. diabetic), ethnic group, etc. Specific printable biomarker sensors can be added to sensor unit 2 and be made optical with specific R codes. Said sensors can also be electrochemical and reference is made to earlier patents from the same author.

Variable IDs that are highly relevant to this technology are found in block code C4, FIG. 9, and include things like location, Wi-Fi nodes associated with a given location, etc. In addition environmental factors (e.g. local temperature, humidity, pollution levels, etc.) are also highly relevant for authentication, grey markets, counterfeits, etc. Specific and proprietary chemistries for both environmental and genomic (e.g. biomarkers) sensors create unique and proprietary tokens that form a unique and novel blockchain platform.

Figure 10:
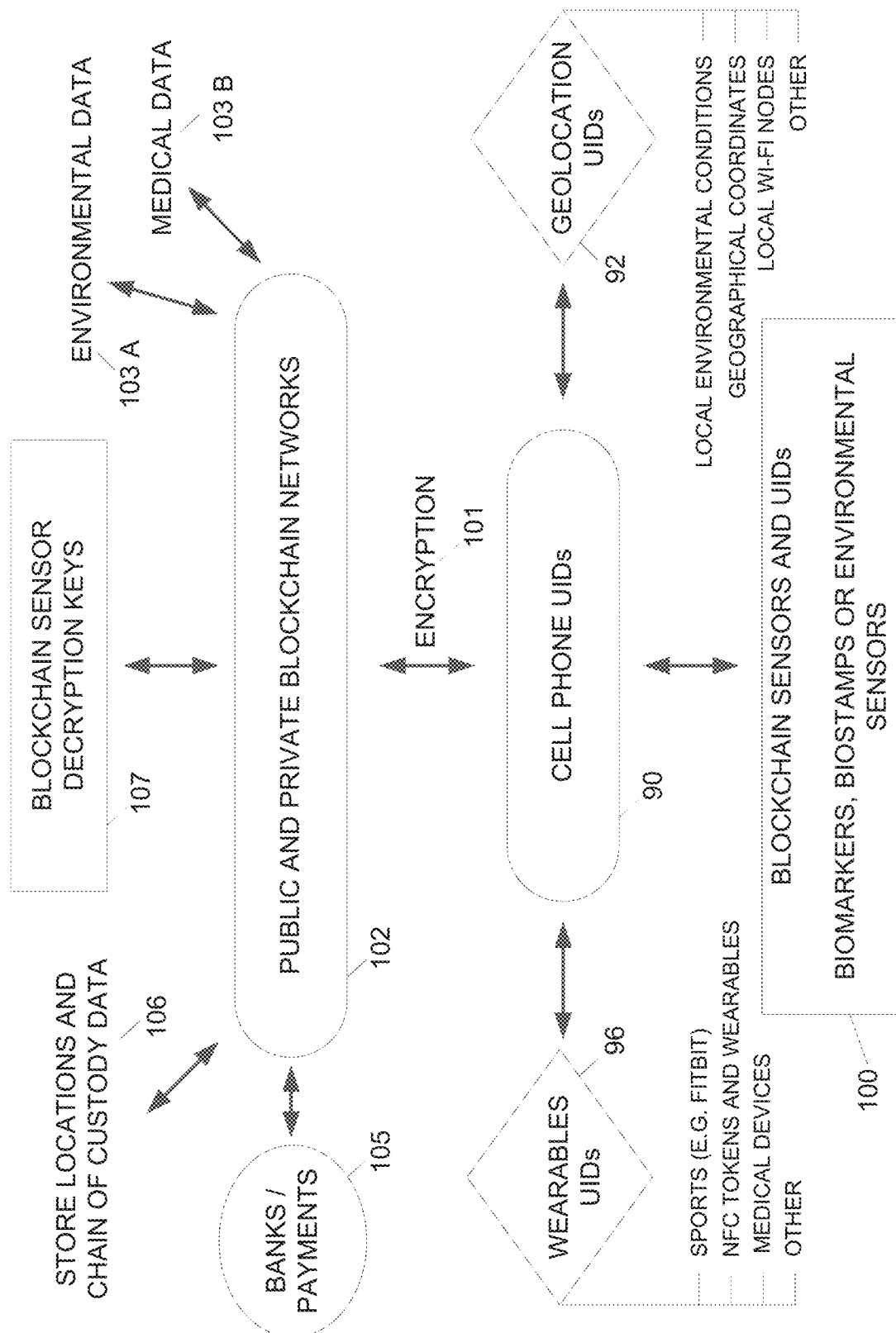
FIG. 10 is a schematic diagram of an example of a complete blockchain sensor network, including payment options according to the present invention.

Referring to FIG. 10, the overall blockchain sensor network system typically comprises:
1) At least one cell phone with a unique identifier code box 90. Each cell phone blockchain sensor transaction is associated with a given location.
2) Customizable blockchain optical sensor units 2 shown in box 100 with unique IDs composed of unique genetic identifiers (biomarkers or biostamps) and/or unique environmental sensors. Said optical sensor units 2 shown in box 100 are typically printable with unique chemistries and typically include printable encryption keys, UIDs and chain-of-custody means.
3) Optional wearable devices with unique IDs box 96 readable directly by said cell phone and typically communicating with said cell phone via NFC, Bluetooth or other wireless or optical means.
4) Geolocation coordinates and associated UIDs box 92 for a given location at the point of reading a blockchain or associated with past blockchain events.
5) An optional encryption process 101 between the cell phone and a wireless network linked to remote servers and databases.
6) Access to private and/or public blockchain networks box 102.
7) Access to local environmental data 103 A associated with said location.
8) Optional access to medical data 103 B associated uniquely with user of said cell phone.
9) Optional access to financial information and payment methods box 105 associated with a given blockchain optical sensor unit Unique ID, a given person and associated public or private blockchains.
10) Chain of custody blockchain data and target item store sale(s) location 106.
11) Access to blockchain decryption keys box 107.

Typically a given company selling a given item has internal proprietary knowledge of the blockchain sensor UIDs and R codes. The company also has the chain of custody blockchain data and the point of sale target location and associated variables. Finally they own the proprietary unique decryption keys for their own blockchain sensors, including the use of unique and proprietary chemistries and the interpretation of the sensor results.

Ledgers, blockchains, are created both on the sensor itself and the chain of custody as explain above and this system creates unique and multiple levels of encrypted unique IDs and unique codes. "Hard" codes include the cell phone UIDs, associated NFC or wearable UIDs, store location UIDs, some biometric data and all the unique codes for the blockchain optical sensor unit. Variable or "soft" codes include environmental data and some variable medical or biomarker data.

Creation of Small Blockchains Networks for Micropayments

The technology combined for example with a Wi-Fi or cell phone (e.g. 5G) network allows for small payments and complete customization of small blockchain sensor networks. Such networks can be easily set up in amusement parks, airports, shopping malls, etc.

Figure 11:
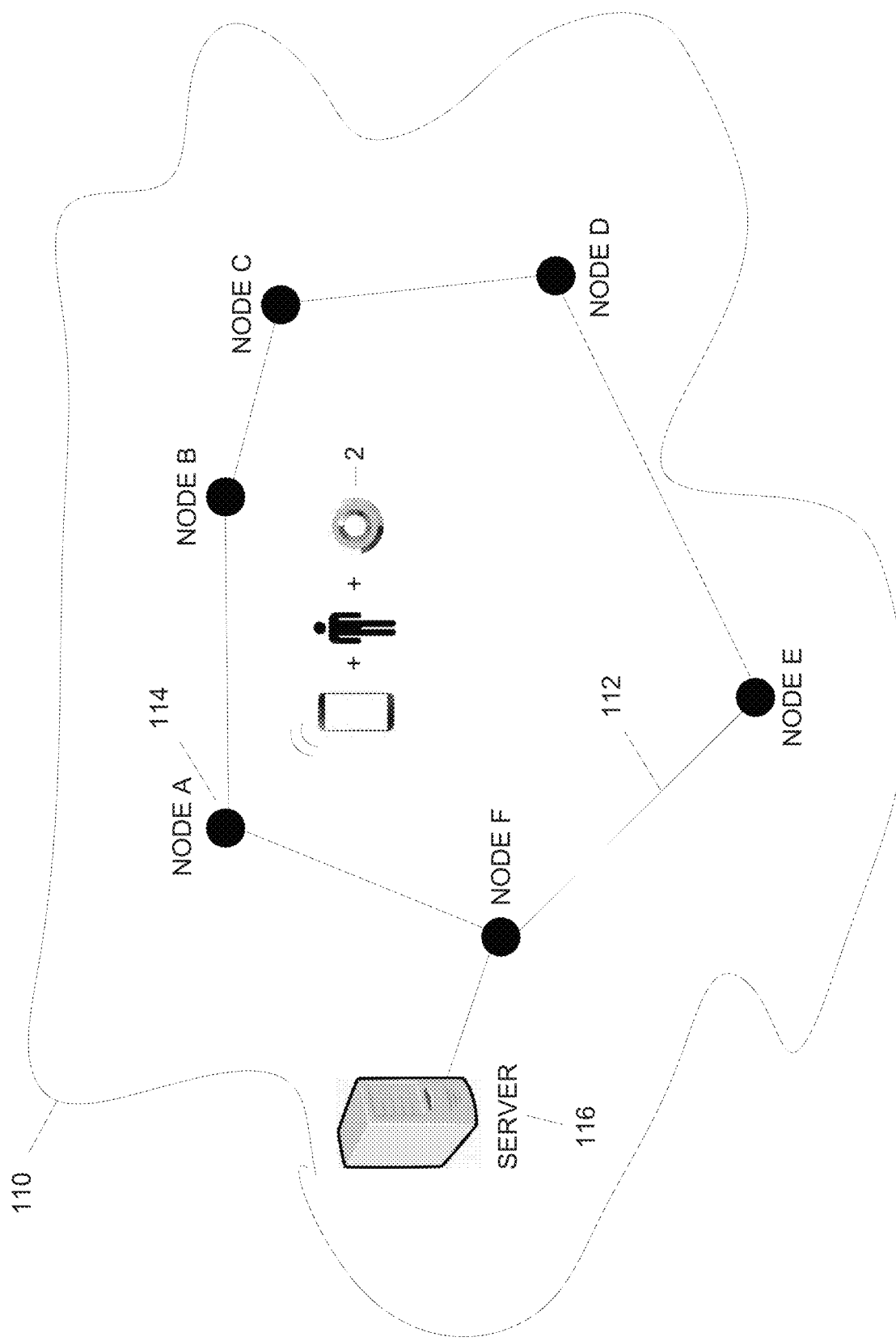
FIG. 11 is a schematic diagram of an example of a small simplified blockchain sensor network in a defined geographical area, e.g. an amusement park, according to the present invention.

Referring to FIG. 11, an amusement park example, in which a park creates an internal secure Wi-Fi network of nodes 114 that span the whole area 110 of the park. Each node 114 has its own unique ID.

The amusement park also has its own printer and server 116. A person receives a day pass that is a blockchain optical sensor unit 2 in the form of a tattoo, a sticker, a wrist band, etc. that contains unique codes R for that day and even that given person. The tattoo can serve as a skin optical sensor 8, for example for UV exposure but also as a form of payment ID for items in the park (e.g. food, special access, etc.). As each customer has its own cell phone with a unique ID and other unique IDs as explained above, these consumer-specific IDs serve as cross-validation in the encrypted network of said amusement park. The entrance fee and set of unique IDs initiates a proprietary closed-loop proprietary blockchain system.

The park creates a blockchain network 112 that reads and authenticates the movement of each given person across the park. Any change or unusual activity can be used to automatically invalidate the ability to make small payments using the sensor unit 2. Sensors can cross authenticate in a number of ways. For example a zone R can have inks with codes that fade. The technology is time-stamped in the park server (when the sticker is printed) and reference colors 12 allow for the degree of fading to be measured precisely.

Passes can be pre-printed with the reference colors 12 and optical sensors 8 and special optical codes added in zone R3 by the park printer. For example codes can be day codes and unique codes linked to a unique phone ID or credit card. Furthermore the amount of credit on the pass can also be encoded. For example a child may have a credit of $20 for the day and use a skin tattoo directly for small payments such as the purchase of an ice cream. NFC can be used to generate part of the codes by simply tapping the phone on a reader at the entrance gate of the park. For example the unique ID of the tag can be matched to the unique ID of the visitor's cell phone or credit card.

Piggyback on Google

Figure 12:
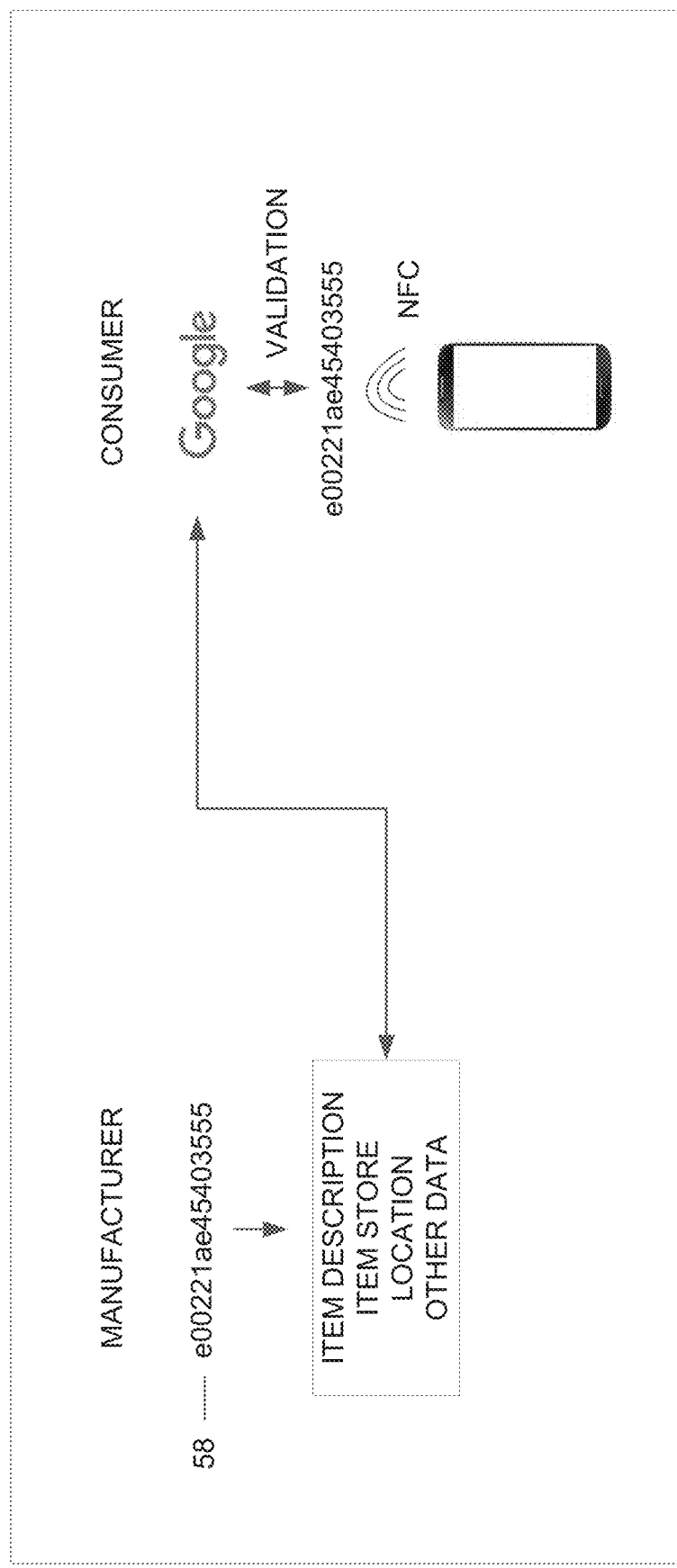
FIG. 12 is a schematic diagram of an example of a simple piggy-back unique ID and authentication system using the Google® search platform according to the present invention.

Blockchain optical sensor units 2 described herein are well suited for piggybacking on global search engines such as Google to create simple and secure authentication networks. This is useful for some applications and markets. For example the unique identification hard ID 58 code from an NFC tag or sensor can become a searchable string on Google as illustrated in FIG. 12.

The manufacturer can associate with the unique ID not only a product description and picture but also the expected sale location (e.g. store, address, country, etc.). This information with the UID can then be made searchable directly by the consumer, as shown in FIG. 12. Expected sale location becomes very useful for counterfeit detection on grey markets. The unique item core hard ID 58, in this instance NFC tag #e00221ae45403555, can also be extended by further unique random numbers or codes, for example manufacturing location, date, etc., as explained above. Since NFC tags can be custom made the model is a bit like the credit card model, where both ownership of the unique magnetic and/or chip codes as well as the manufacturing and distribution of the card are key factors. Market applications include for example cosmetics and wines.

The use of the simple "piggy back" technology on a secure public IT platform does not preclude other applications and the use of sophisticated blockchains as multiple unique IDs are created from the onset.

How the Technology Works

As described above there are several possible ways to proceed according to the present invention. Web links for blockchain optical sensor unit 2 can be encoded optically or in the wireless NFC chip, or both.

As a consumer approaches the blockchain optical sensor unit 2 with his or her cell phone, an option is given to download an app by the reading of the initial initiator optical web information encoded on the label and/or reading the initial web link in the NFC tag. This then initiates the blockchain sensor technology. The consumer can then learn about the product, authenticate it, read the sensors, access any related blockchain network, make payments and apply health functions, as described more fully below.

Facebook programs such as Messenger can already directly read optical codes. Many other similar programs are available and reading a bar or a QR code 136 or NFC directly with cell phones is now very common and can be used as initiators. Therefore many users will be able to start using the technology without having to download an app. A web link to a customized network can therefore be printed directly on the item. The purpose of this invention is to add printable optical sensors 8, traceability, unique chain of custody sensors and identification, unique person ID via custom biomarker codes, unique environmental signature codes, custom blockchains, etc. to greatly enhance the opportunity created by the sophisticated camera in cell phones for global IoT, payments and consumer health applications. The technology allows for example a small payment with a disposable blockchain skin tattoo that also monitors skin health.

Printable optical sensors allow this technology to be customized to almost any market or consumer application. The technology incorporating the optical sensor unit 2 can be made in the form of a skin tattoo, a skin patch, a sticker, a stand-alone sensor, a card, a product label, a food label, a lateral flow immunoassay or can be incorporated into virtually any item (e.g. foods, luxury goods, medical industry, etc.). The technology, when combined with NFC can also be embedded into items since sensors can be passive (battery-less) and NFC reads through water. In some instances an NFC tag or sensor can be embedded in an item and the matching optical sensors 8 printed as a separate matching label or sticker with its own unique set of IDs.

With minor modifications the technology can be read directly with applications such as Messenger from Facebook or any custom app on any smart cell phone.

This technology takes elements from blockchain technology but simplifies them, adds printable optical sensor unit 2 functionality and unique person specific codes, and allows great flexibility in the use of small encrypted networks.

Flexibility in the Uses of Blockchain

The system described here allows for great flexibility in the uses of blockchain. Typically a unique optical code R forming a part of sensor unit 2, a unique wireless hard ID 58 part of the ASIC 52, a QR or other similar codes are used to start a blockchain.

However the technology allows great flexibility in the uses of the UIDs shown in the figures and the creation of later stage blockchains, simplified blockchains and reverse blockchains.

Figure 17:
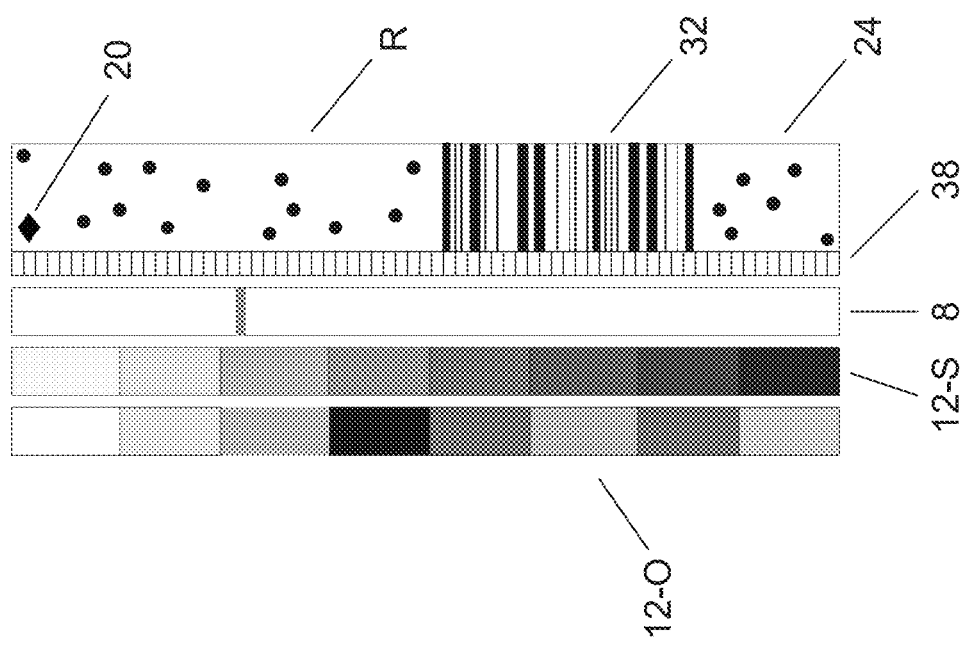
FIG. 17 shows an example of a printable blockchain optical sensor for lateral flow immunoassays to authenticate, read and detect biomarkers via a blockchain network according to the present invention.

For example in the medical diagnostic and pharmaceutical markets a blockchain can be initiated by the initial read of a drug or skin patch, see FIG. 8 in combination with FIGS. 6 and 17. As an illustration in a clinical trial application for a given patient using a new drug a new blockchain can be initiated for that patient and drug and form a part of a precision diagnostics medical record for a given person and given genome.

Figure 13:
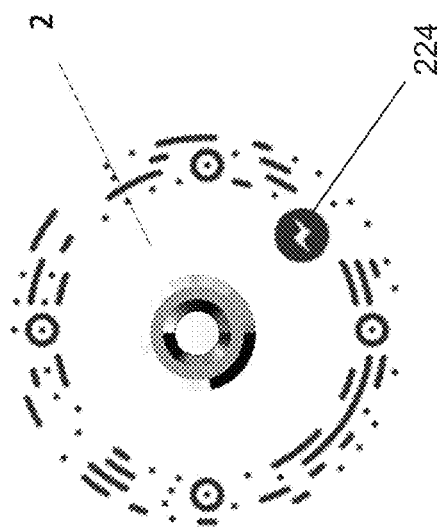
FIG. 13 is an illustration of a printable blockchain optical sensor combined with a Facebook Messenger® code according to the present invention.

Another example and referring to FIG. 13 is the reading of an environmental threat sensor via Facebook Messenger. The UID of a given cell phone and given location can initiate a blockchain of sensor events, linking the location, user, environmental data, progression of the treat, etc. in a blockchain. Similarly a payment or payment credit system can be created by an initial read of an optical sensor unit 2 for given applications, one of which is described in FIG. 11.

APPLICATION EXAMPLES AND SOME EMBODIMENTS FOR THE TECHNOLOGY

Note: For the purpose of clarity some of the examples below do not show optical R codes described in detail above.

Cosmetics and Skin Care

Example 1

A global company with multiple skin care brands wants to use the same type of optical sensor unit for example for UV/sun exposure for each brand. In this example the optical sensor unit is the same and some of the optical codes R are modified so that each brand has its own web links built into the same blockchain optical sensor unit 2. The technology can work stand-alone or with a platform such as Facebook Messenger, allowing optical reading while broad distribution of the sensor units 2 can be done by the brands, each with their own web links. FIG. 13 shows how the printable blockchain optical sensor unit 2 can be incorporated directly within a Facebook Messenger code 224 and serve both as an optical sensor 8 and a social media optical link. The optical sensors can be packaged as a bundle with a skin care product made by the company. Beyond UV exposure another concern for cosmetics companies is pollution and an application example is a printable pollution detection optical sensor 8 and use of social media, via the code 224, to communicate to others a local environmental threat or condition of pollution or other environmental variables. Optical sensors 8 can visually warn a user of a given threat as well as threat level. Note: the optical codes in sensor unit 2 of FIG. 13 are not shown for the sake of clarity and can be omitted in some applications.

Example 2

Figure 2:
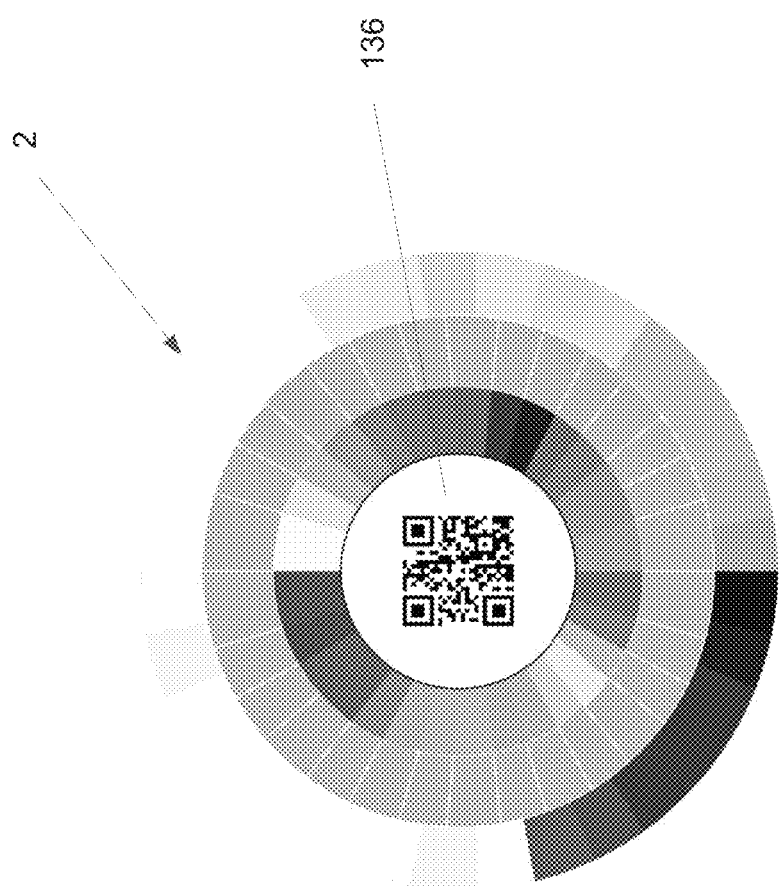
FIG. 2B shows the same sensor technology as FIG. 2A but with an added QR code for sensor orientation and to form a web link according to the present invention.
Figure 14:
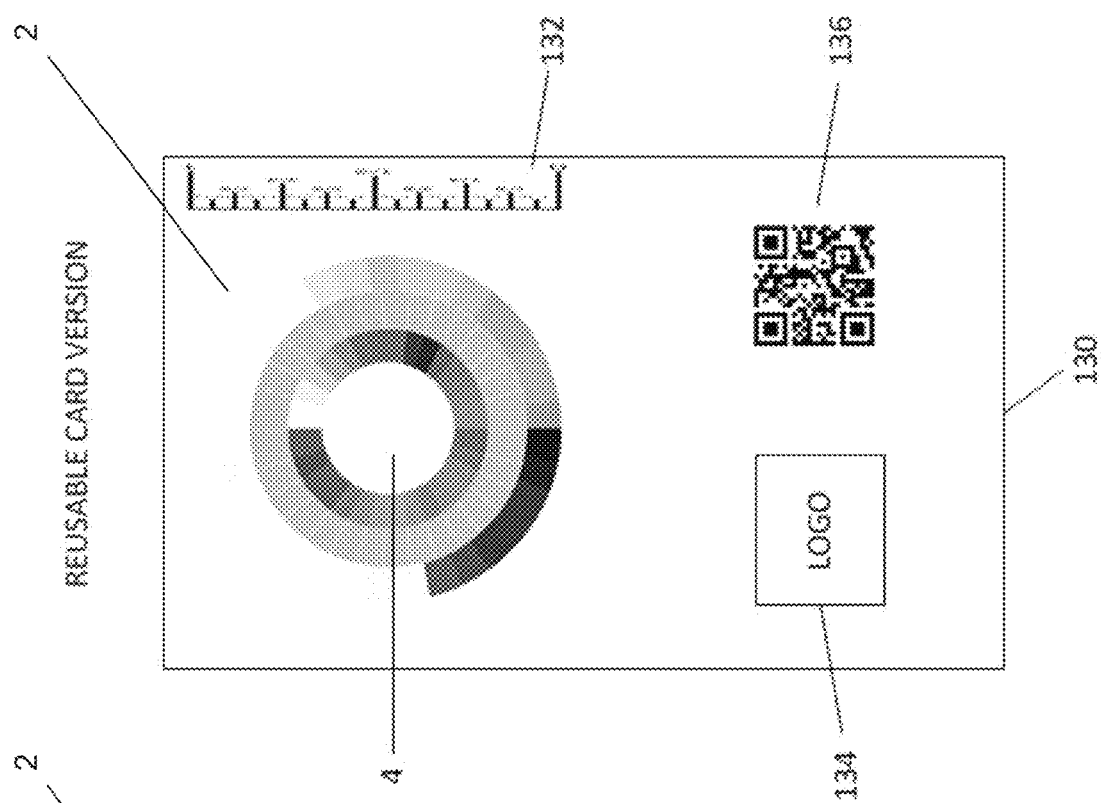
FIG. 14A and FIG. 14B are examples of a printable blockchain optical sensor for a skin cancer, melanoma, detection application.
Figure 14:
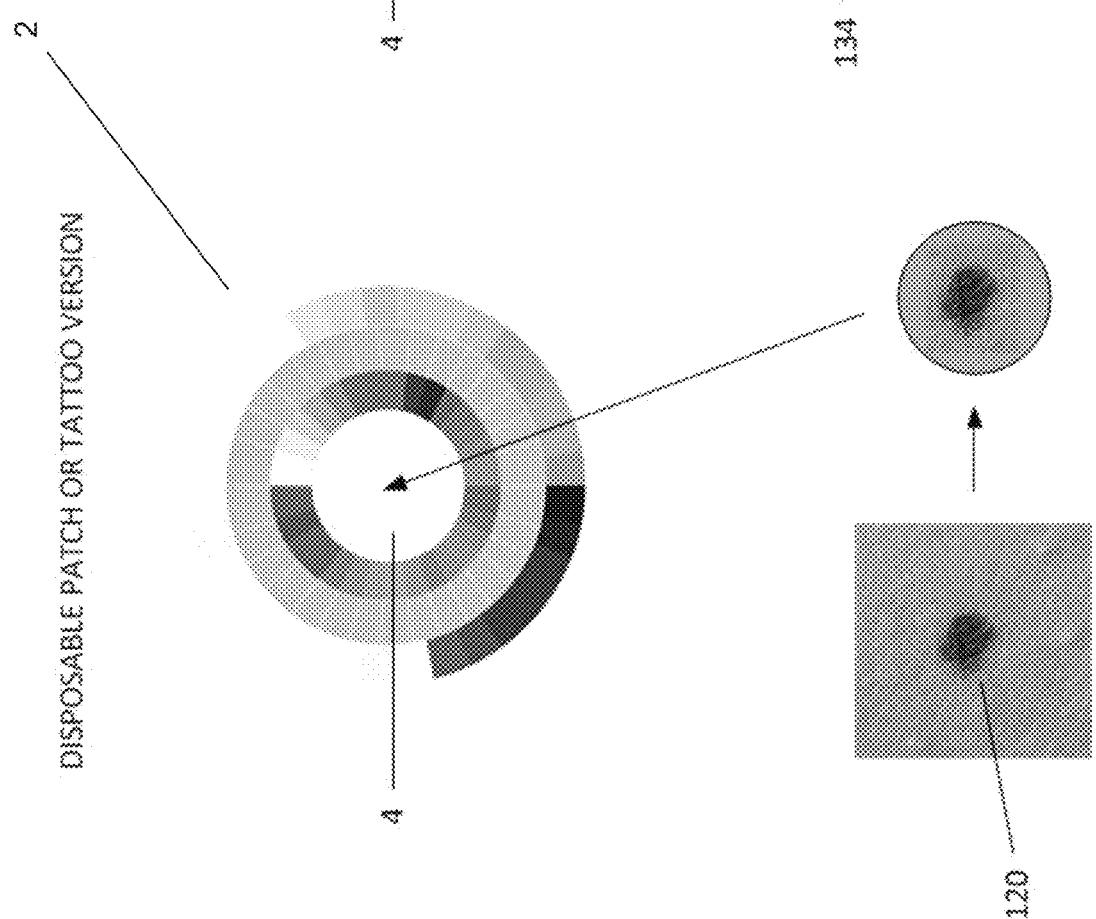
Figure 15:
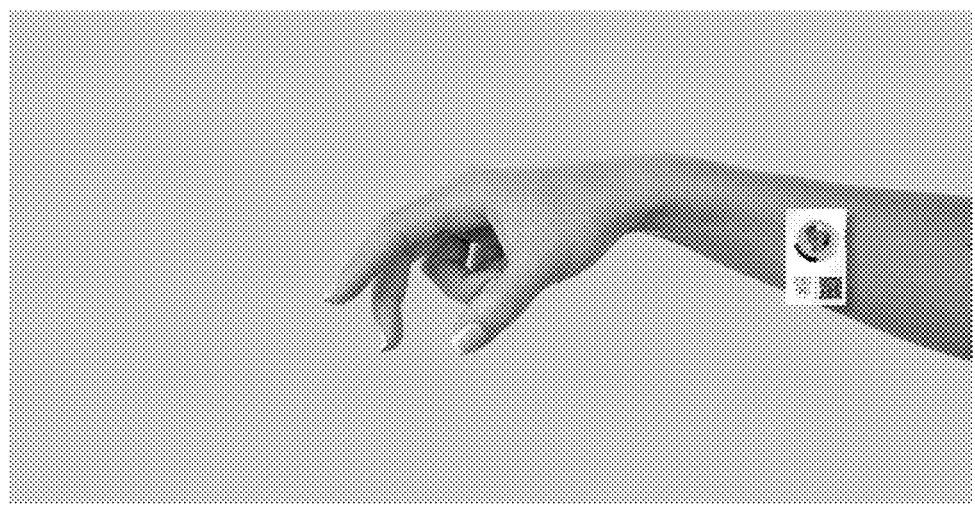
FIG. 15 is a further illustration of the application of FIG. 14B onto a human arm according to the present invention.

Referring to FIGS. 14A, 14B and 15, the sensor unit 2 is modified to serve as a melanoma checker. In the example of 14B the universal printable blockchain optical sensor unit 2 is printed on a card or plastic stock that serves as a reusable melanoma checker. Alternatively the mole checker is made in the form of a skin tattoo as shown in FIG. 14A. The skin mole 120 is covered by either device and appears in opening 4. As explained in FIG. 2, sensor unit 2 contains both ambient light correction reference colors 12 and skin tone (Pantone®) reference colors. This is very important since the specific colors and tones of the mole can be determined in addition to the patterns and shape of the lesion, if the mole is in fact a potential melanoma.

In the case of the reusable card 130, a ruler 132 can be added as well as an area for a company or distributor logo 134 and a QR code 136 or a bar code. Alternatively, either technology can include NFC and printable optical R codes, not shown.

The reference colors for skin and ambient light allow precise quantification of skin tone and mole color(s). As shown in FIG. 15, the card from FIG. 14B is simply placed over a mole and a picture is taken. Remote interpretation is then done by a doctor. Alternatively algorithms are created as an app for mole shape, density and color patterns to flag out suspicious moles.

The technology can include a UV sensor and other sensors, secure database of past moles and changes to these moles, links to online medical consultation and direct payment. The technology described in FIGS. 14A, 14B and 15 can also apply just to skin tones, an important market for cosmetic companies.

Micro-Payments and More Secure Currency

Figure 16:
FIG. 16 shows addition of a printable blockchain optical sensor into currency, a twenty dollar bill, according to the present invention.

The blockchain optical sensor unit 2 technology can be incorporated into bank cards, credit cards or directly into currency, see FIG. 16, to allow cross validation of codes, incorporation of sophisticated unique ID methods (e.g. DNA), sensors that are heat sensitive, sensitive to certain environments or sensitive to specific currency validation chemistries for example in a pen, etc. For example the twenty dollar bill in FIG. 16 can include as part of optical sensor unit 2 environmentally sensitive inks with color references and codes, where the local environmental conditions such as temperature, moisture, UV, etc. can be used as a cross validation means. As described above a temperature sensitive ink that responds to the touch of a finger can also be used to reveal a unique code, key or pattern that can be used to cross validate the currency. Time changing inks in combination with other printable sensors, unique chemistries and codes can be particularly useful for incorporation into printable currency.

Micro-payment networks have been explained above for one application, FIG. 11. However this technology can be combined with and enhance any existing payment system such as Apple Pay®, Paypal®, Visa®, Master Card®, etc. or alternatively private sensor blockchains can be created directly between a consumer company and their individual customers. Large consumer or Pharmaceutical companies can associate these sensors with product authentication, resupply, payments etc.

Food and Produce

Food freshness blockchain optical sensor units 2 in labels can be applied to either the outside or inside of a meat, fish or produce package. Reference is made to U.S. Pat. No. 10,271,738 that is incorporated herein by reference in its entirety.

In case the sensor unit 2 is on the outside it can include microneedles 70 that can be depressed on the package to bring a small amount of surface fluid into an optical sensor 8. Sensor 8 can indicate by a color change the freshness of the food in the package.

In case the sensor unit 2 label is printed on the inside it can include optical sensors 8 for detecting the presence of bacteria or specific metabolites of bacteria, the presence of certain gases, the past storage temperature (e.g. thresholder optical temperature sensors), etc.

The package also includes blockchain shipping information, origin, etc.

Jewelry and Beauty

Sensor units 2 can be incorporated into labels that can be made in the form of jewelry. For example a skin sensor unit 2 can be made in the form of a jewelry skin tattoo with "gold" combined with colorful sensors and patterns. Such technology is disposable and typically is for use only for a day or a few days. A blockchain optical sensor unit tattoo can also be used for small local payments.

In more permanent applications and including NFC, passive sensor smart jewelry can include a universal payment key and battery-less sensors (e.g. temperature, UV), etc.

Cross validation of sensor data and unique codes is done with the cell phone.

For example a jewelry piece (e.g. a necklace) can include a NFC sensor with a unique ID and a series of optical sensors 8 including those to detect temperature, UV sun exposure and environmental sensors that can be custom made to a specific geography or even to a specific genome of an individual, see U.S. Pat. No. 6,031,454 from the same author. The technology can also become a specific medical sensor unit 2 such as an asthma prevention sensor, see U.S. Pat. Nos. 7,109,859 and 7,518,504 from the same author. These sensors can be battery-less and be included in a lapel pin, a pendant, etc. Sensors and color patterns can create both functional and visually pleasing jewelry blockchain optical sensor units 2. In fact R codes can themselves form a part of the design.

Geolocation of the cell phone and time stamps can precisely locate the cell phone and assess indoor or outdoor location. Environmental parameters can then be taken and authenticate the blockchain transaction based on sensor data, location and cross validation of the unique IDs (cell phone and NFC or Bluetooth).

Therefore smart jewelry can be used not only to gather sensor and health data but also for payments.

Pharmaceutical and Biomarker Tests

Example 1

A blockchain optical sensor unit 2 with a temperature sensitive optical sensor 8 in the form of a label is attached to a heat sensitive drug or vaccine. If the drug was not stored properly or was tampered with this would be immediately detectable at the point of use. Important current markets include biosimilars and biologics (e.g. Humira).

Example 2

An example of an application for the pharmaceutical industry is a printable drug interaction sensor unit 2 that includes a specific optical sensor 8 for specific markers (biomarkers) that indicate either that a given drug is working or can indicate a negative drug interaction or toxicity. The technology can be used for both diagnostics and drug compliance and has broad market applications beyond the pharmaceutical industry.

For example the sensor unit 2 can have an optical sensor 8 that can be dipped into a urine sample in a way similar to a lateral flow immunoassay currently used for common pregnancy tests, however in this example the lateral flow assay would detect other biomarkers of interest.

The sensor unit 2 can include all the functionality described above, can incorporate NFC and be electronic or be a low cost optical blockchain optical sensor unit 2 combined with a simple lateral flow immunoassay, as shown in FIG. 17.

The technology is quantitative, printable, low cost, has authentication and web communication means and can apply to almost any protein or biological test within minutes.

In FIG. 17, item 12-O is the optical reference colors, item 12-S the reference colors for the immunoassay, the optical sensor 8, in this case a lateral flow immunoassay, item 38 is the position marker and the other items are as described above such as R codes, keys, etc.

An application example is biomarker detection, resupply of the drug and payment. Specifically as applied to the pharmaceutical industry market, the disposable test is included with a given medication and can serve as a home companion diagnostics test, or a test for a given medical condition, a test for specific biomarkers, a test for drug compliance, or a combination of these tests and can include blockchain authentication, resupply and payment means.

Luxury Goods

Figure 18:
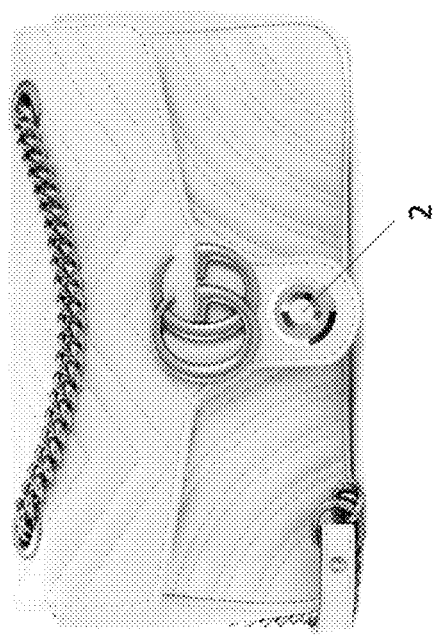
FIG. 18 shows an example of a printable blockchain optical sensor combined with a luxury good according to the present invention.

Blockchain optical sensor units 2 can be inserted in luxury goods as NFC tags or sensors and can also be used as optical sensors 8 for determining environmental exposures, as explained above. For example in FIG. 18 a luxury brand item can be fitted with a blockchain optical sensor unit 2 with durable inks that can authenticate the item and provide sensor information as a decorative logo. Alternatively an NFC sensor can also be used or can be combined with the optical sensors, see combined unit 55 in FIG. 4. The unique IDs allow a reduction of grey markets, authentication, sensing and payments.

Health and Medical Applications

Blockchain optical sensor units 2 have substantial implications across the entire medical, health and diagnostics fields. The sensor units 2 can be overlaid as stickers or labels on most existing tests or devices to add a new level of security and authentication.

New types of diagnostic sensors 8 can also be created with this technology. For example FIG. 6 above shows how a painless diabetes patch with optical sensors 8 can be created by the combination of microneedles 70 and customized blockchain codes and optical sensors 8.

Specifically the diabetes patch contains microneedles 70, optical light correction reference colors and sensor reference colors 12, and an optical sensor 8 with specifically formulated optical chemistries to quantify glucose levels in the interstitial fluid. The patch can also contain other optical biomarker sensors 8 and sensors 8 for temperature, skin moisture levels, etc.

The patch is depressed onto the skin and then read with the camera of the cell phone.

The printable diabetes patch can also contain R codes for authentication and web links, links to medical help, etc. (not shown).

This optical technology complements the electro-chemical diabetes patch descried in U.S. Pat. No. 8,077,042.

Figure 19:
FIG. 19 shows an example of a health monitoring biostamp patch for biomarker and blockchain applications according to the present invention.
Figure 20:
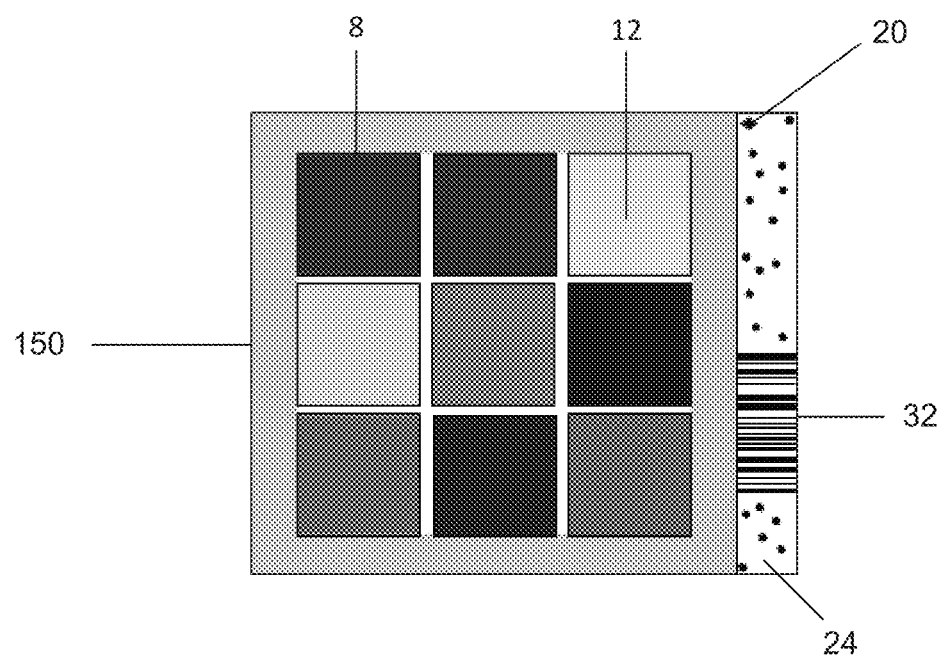
FIG. 20 shows an example of a printable blockchain optical sensor biostamp for biomarker and person identification according to the present invention.

Medical, pharmaceutical and biomarker blockchain optical sensor units 2 can also be in the form of printable biostamps 150 as illustrated in FIG. 19. These are specific chemistries that are printed directly in arrays on a substrate such as a skin patch, a card, or a cassette and react to different cues such as biomarkers in sweat, interstitial fluid or urine to create unique optical patterns. These patterns can include permanent reference colors, which are themselves arranged in a unique proprietary pattern forming a unique code, like a QR code. The combination creates person-specific or genomic printable blockchain optical sensor units 2 and tokens. Such include sensors 8 that can be used for diagnostic and pharmaceutical applications and can also be used to authenticate uniquely a person by the creation of unique patterns on the biostamp resulting from the unique chemistries and biomarkers of each person or specific genome. The arrays can contain specific chemistries acting as receptors for specific biomarkers associated with specific conditions (e.g. diabetes) as well as chemistries to discover new biomarkers or chemistry associations. As a large number of different chemistries can be printed on a single biostamp array this technology can be used for advanced diagnostics, pharmaceutical applications and biomarker discovery. FIG. 20 shows how a printable chemical biostamp can be combined with a proprietary optical coding system and forming a variation of sensor unit 2 from FIG. 1. The biostamp blockchain optical sensor unit 150 technology can be combined with environmental or biomarker sensors 8, reference colors 12, orientation and size reference 20, encryption key 24, bar code 32 and other sensors or codes as described above. In the form of a card or cassette it can be dipped in urine to conduct an advanced diagnostic biomarker or drug compliance test using as one of the optical sensors 8 a multiplex lateral flow immunoassay. The technology has broad market applications for asthma prevention, drug biomarkers and compliance, environmental sensors, person authentication, biomarker discovery and a combination of these markets.

IoT

The technology applies universally to almost any Internet of Things (IoT) market or application.

Grey Markets and Counterfeits

The technology applies universally to any consumer good or any Pharmaceutical (drugs) for gray market detection, which is sale of an item that should not be sold in a given location and to help detect counterfeits.

Geolocation is a key aspect for detection of grey market sales and comes from the consumer cell phone. Specific environmental blockchain sensors 8 can cross validate with the local environmental conditions, precise geolocation allows individual store identification and UIDs and tokens uniquely authenticate the item. For example if a UV blockchain sensor 8 on the good indicates high sun exposure and the item is expected to be sold in a location where the real time conditions indicate a cloudy or rainy day via the cell phone, then a likely grey market event is detected. Environmental blockchain sensors can be very sophisticated and include air quality and the detection of given chemicals, physical conditions, etc.

Conventional blockchain can be used in this instance and the last chain of identification comes from the consumer reading and authenticating the entire chain as explained above.

CONCLUSION

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breath and scope of the present invention should not be limited by any of the above-described exemplary embodiments, but should be defined only in accordance with the following claims and their equivalents.

I claim:

1. A skin patch for detecting patient compliance with a pharmaceutical treatment protocol for a specific pharmaceutical comprising:
   a printable blockchain optical sensor unit comprising: at least one optical sensor, a first plurality of permanent reference colors, an identification code, a central hole, an orientation reference and an adhesive configured to removably secure said patch to a skin of a person;
   wherein said optical sensor is configured to measure an application by the person of the specific pharmaceutical inside the central hole; and
   wherein an output from said optical sensor unit is configured to be uploaded to a blockchain network by a wireless reader.

2. The skin patch for detecting the patient compliance with the pharmaceutical treatment protocol for the specific pharmaceutical according to claim 1 wherein said optical sensor unit is combined with a Near Field Communication sensor unit comprising a chip with a unique identification code, an antenna and a sensor functionality that includes at least one of the following sensors: a thermistor sensor capable of measuring a skin temperature, a pressure sensor configured to measure skin pressure, a stretch sensor configured to measure stretching of skin adjacent to said stretch sensor, an electro-chemical sensor configured to measure a presence of and to quantify an amount of a specific chemical or biomarker and combinations thereof; and wherein application of said specific pharmaceutical inside said central hole is detectable by the output from at least one of said thermistor measuring a change in the skin temperature following application, said pressure sensor measuring a change in the skin pressure following application, said stretch sensor measuring stretching of the skin adjacent to said stretch sensor following application or said electro-chemical sensor measuring the presence of the specific chemical or biomarker associated with said application of said specific pharmaceutical.

3. The skin patch for detecting the patient compliance with the pharmaceutical treatment protocol for the specific pharmaceutical according to claim 1 wherein said specific pharmaceutical is selected from the group consisting of adalimumab, etanercept, dupilumab, mepolizumab, benralizumab, reslizumab, and biosimilars or biologic equivalents of these pharmaceuticals.

4. The skin patch for detecting the patient compliance with the pharmaceutical treatment protocol for the specific pharmaceutical according to claim 1 wherein said wireless reader is a cellular phone.

5. The skin patch for detecting the patient compliance with the pharmaceutical treatment protocol for the specific pharmaceutical according to claim 1 wherein said optical sensor unit further comprises a plurality of additional optical sensors, a first plurality of said additional optical sensors which each reacts with at least one pre-determined chemical or biomarker after application of said pre-determined pharmaceutical and wherein an output of each of said first plurality of said additional optical sensors and said identification code forms a user-specific pattern of data that is configured to be uniquely associated with a user following uploading of said outputs to said blockchain network.

6. The skin patch for detecting the patient compliance with the pharmaceutical treatment protocol for the specific pharmaceutical according to claim 1 wherein said optical sensor unit further comprises an additional identification code and wherein said additional identification code is configured to be used to authenticate a payment associated with said skin patch to said blockchain network.

7. A method for monitoring patient compliance with a pharmaceutical treatment protocol for a specific pharmaceutical comprising the steps of:
a) providing a skin patch comprising a printable blockchain optical sensor unit comprising at least one optical sensor, a first plurality of permanent reference colors, at least one unique identification code, a central hole, an orientation reference and an adhesive configured to removably secure the sensor unit to a skin and wherein said at least one optical sensor is configured to measure an injection of said specific pharmaceutical following injection of said specific pharmaceutical inside said central hole;
b) directing a user to secure said skin patch to the skin of said user at a planned injection site;
c) directing said user to inject said specific pharmaceutical into said central hole;
d) detecting the injection of said specific pharmaceutical by monitoring a change in an optical property of said at least one optical sensor following injection of said specific pharmaceutical;
e) directing said user to take a picture of said skin patch using a wireless reader after injection of said specific pharmaceutical; and
f) said wireless reader uploading said picture to a blockchain network.

8. The method for monitoring the patient compliance with the pharmaceutical treatment protocol for the specific pharmaceutical according to claim 7 wherein step a) further comprises providing said optical sensor unit in combination with a Near Field Communication sensor comprising a chip, a unique identifier, an antenna and a sensor functionality that comprises at least one of a thermistor capable of measuring a skin temperature, a pressure sensor capable of measuring skin pressure, a stretch sensor configured to measure stretching of skin adjacent to said stretch sensor or an electro-chemical sensor configured to measure a presence of a specific chemical or biomarker associated with said injection of said specific pharmaceutical; and wherein step f) further comprises said wireless reader uploading an output from said Near Field Communication sensor to said blockchain network.

9. The method for monitoring the patient compliance with the pharmaceutical treatment protocol for the specific pharmaceutical according to claim 7 wherein step e) further comprises associating said picture with the at least one unique identification code of said optical sensor unit and step f) further comprises uploading a combination of said picture and said at least one unique identification code to said blockchain network.

10. The method for monitoring the patient compliance with the pharmaceutical treatment protocol for the specific pharmaceutical according to claim 9 wherein said wireless reader has a unique identification code and wherein step f) further comprises associating said at least one unique identification code of said optical sensor unit and said unique identification code of said wireless reader with said picture when uploading said picture to said blockchain network.

11. The method for monitoring the patient compliance with the pharmaceutical treatment protocol for the specific pharmaceutical according to claim 9 wherein step f) further comprises determining a geolocation of said wireless reader and associating said geolocation of said wireless reader with said unique identification codes when uploading said picture to said blockchain network.

12. The method for monitoring the patient compliance with the pharmaceutical treatment protocol for the specific pharmaceutical according to claim 10 wherein step a) further comprises providing on said optical sensor unit a link to said blockchain network and wherein in step f) said wireless reader uses said link to upload said picture to said blockchain network.

13. The method for monitoring the patient compliance with the pharmaceutical treatment protocol for the specific pharmaceutical according to claim 7 wherein step a) comprises providing the printable blockchain optical sensor unit comprising a plurality of optical sensors, wherein in step b) a first plurality of the plurality of optical sensors each of which reacts with at least one pre-determined biomarker after securing of said skin patch to the skin and wherein an output of said first plurality of the plurality of optical sensors and said at least one unique identification code form a user-specific pattern of data that is configured to be uniquely associated with the user during uploading of said picture to said blockchain network in step f).

14. The method for monitoring the patient compliance with the pharmaceutical treatment protocol for the specific pharmaceutical according to claim 7 wherein step a) further comprises providing the printable blockchain optical sensor unit with an additional unique identification code and wherein said additional unique identification code is configured to be used to authenticate a payment associated with said optical sensor unit to said blockchain network.

15. An addressable blockchain optical sensor unit device that is readable with a cellular phone associated with a network comprising:
- an optical sensor unit comprising at least one lateral flow immunoassay forming an optical sensor on a substrate, a plurality of permanent reference colors, an identification code and an orientation reference;
- wherein an output from said at least one optical sensor is configured to be authenticated and uploaded to a blockchain network by the cellular phone utilizing said identification code; and
- wherein said addressable blockchain optical sensor unit measures at least one of a protein, a metabolite, a toxin, a pathogen, a biomarker associated with a health condition, a biomarker associated with a use of a specific drug, or a combination thereof.

16. The addressable blockchain optical sensor unit device as recited in claim 15 wherein said optical sensor unit further comprises a first encryption key.

* * * * *